United States Patent
Leipzig et al.

(10) Patent No.: US 9,020,476 B2
(45) Date of Patent: Apr. 28, 2015

(54) SYSTEM AND METHOD FOR REMOTE CARE AND MONITORING USING A MOBILE DEVICE

(75) Inventors: Gordon I. Leipzig, Deerfield, IL (US); Pranav U. Srivastava, Chicago, IL (US)

(73) Assignee: Leipzig Technology, LLC, Deerfield, IL (US)

( * ) Notice: Subject to any disclaimer, the term of this patent is extended or adjusted under 35 U.S.C. 154(b) by 149 days.

(21) Appl. No.: 13/612,368

(22) Filed: Sep. 12, 2012

(65) Prior Publication Data

US 2013/0065569 A1  Mar. 14, 2013

Related U.S. Application Data

(60) Provisional application No. 61/533,600, filed on Sep. 12, 2011.

(51) Int. Cl.
| | |
|---|---|
| H04W 24/00 | (2009.01) |
| H04W 4/16 | (2009.01) |
| H04W 4/00 | (2009.01) |
| G06F 19/00 | (2011.01) |
| H04M 1/725 | (2006.01) |
| G06F 9/44 | (2006.01) |
| H04L 12/24 | (2006.01) |
| H04L 29/08 | (2006.01) |
| A61B 5/00 | (2006.01) |
| A61B 5/11 | (2006.01) |

(52) U.S. Cl.
CPC ........... *H04W 4/001* (2013.01); *H04L 41/0879* (2013.01); *H04L 41/5064* (2013.01); *H04L 67/22* (2013.01); *G06F 19/3418* (2013.01); *H04M 1/72536* (2013.01); *H04M 1/72588* (2013.01); *A61B 5/6898* (2013.01); *A61B 5/747* (2013.01); *A61B 5/0022* (2013.01); *A61B 5/1112* (2013.01); *A61B 5/1117* (2013.01); *G06F 19/3456* (2013.01); *H04L 67/125* (2013.01); *H04L 67/12* (2013.01); *G06F 9/4446* (2013.01)

(58) Field of Classification Search
CPC ................................. H04W 4/04; H04W 4/08
USPC ......................................... 455/416, 419, 420
See application file for complete search history.

(56) References Cited

U.S. PATENT DOCUMENTS

| | | | |
|---|---|---|---|
| 7,257,387 B2 * | 8/2007 | Laliberte | 455/404.1 |
| 7,565,132 B2 * | 7/2009 | Ben Ayed | 455/404.1 |
| 2006/0119468 A1 * | 6/2006 | Van Swaay | 340/5.1 |
| 2010/0029261 A1 * | 2/2010 | Mikkelsen et al. | 455/419 |
| 2011/0065419 A1 * | 3/2011 | Book et al. | 455/411 |
| 2012/0149353 A1 * | 6/2012 | Helfrich | 455/418 |
| 2013/0040629 A1 * | 2/2013 | Sprigg et al. | 455/419 |

\* cited by examiner

*Primary Examiner* — Qun Shen
(74) *Attorney, Agent, or Firm* — Levenfeld Pearlstein, LLC

(57) ABSTRACT

A system and method for remote care and monitoring of the user of a mobile device, such as a smartphone, and for simplifying use of the mobile device by the user. The system and method comprises software, operable on the mobile device and/or a remote device (such as another smartphone, a computer (including, for example, a web-based application system) or other device), for facilitating the use of a mobile smartphone device while also enabling authorized users (e.g. care providers) to remotely interact with the mobile user, provide them medical care information, daily care instruction, immediate connectivity, mobile phone control and tracking functions, general assistance as well as remotely updating and maintaining the mobile user's mobile device.

20 Claims, 23 Drawing Sheets

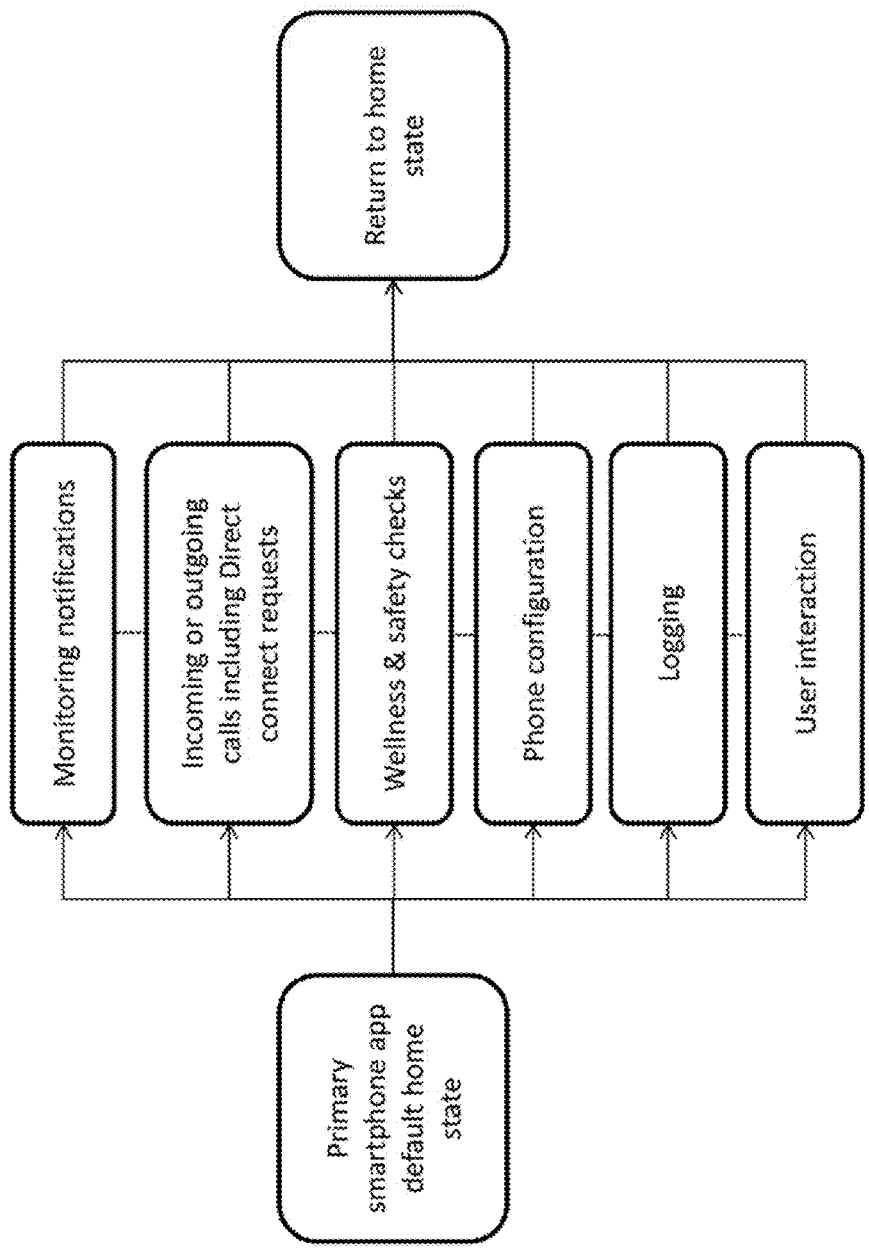
FIG. 15: Overall possible state changes

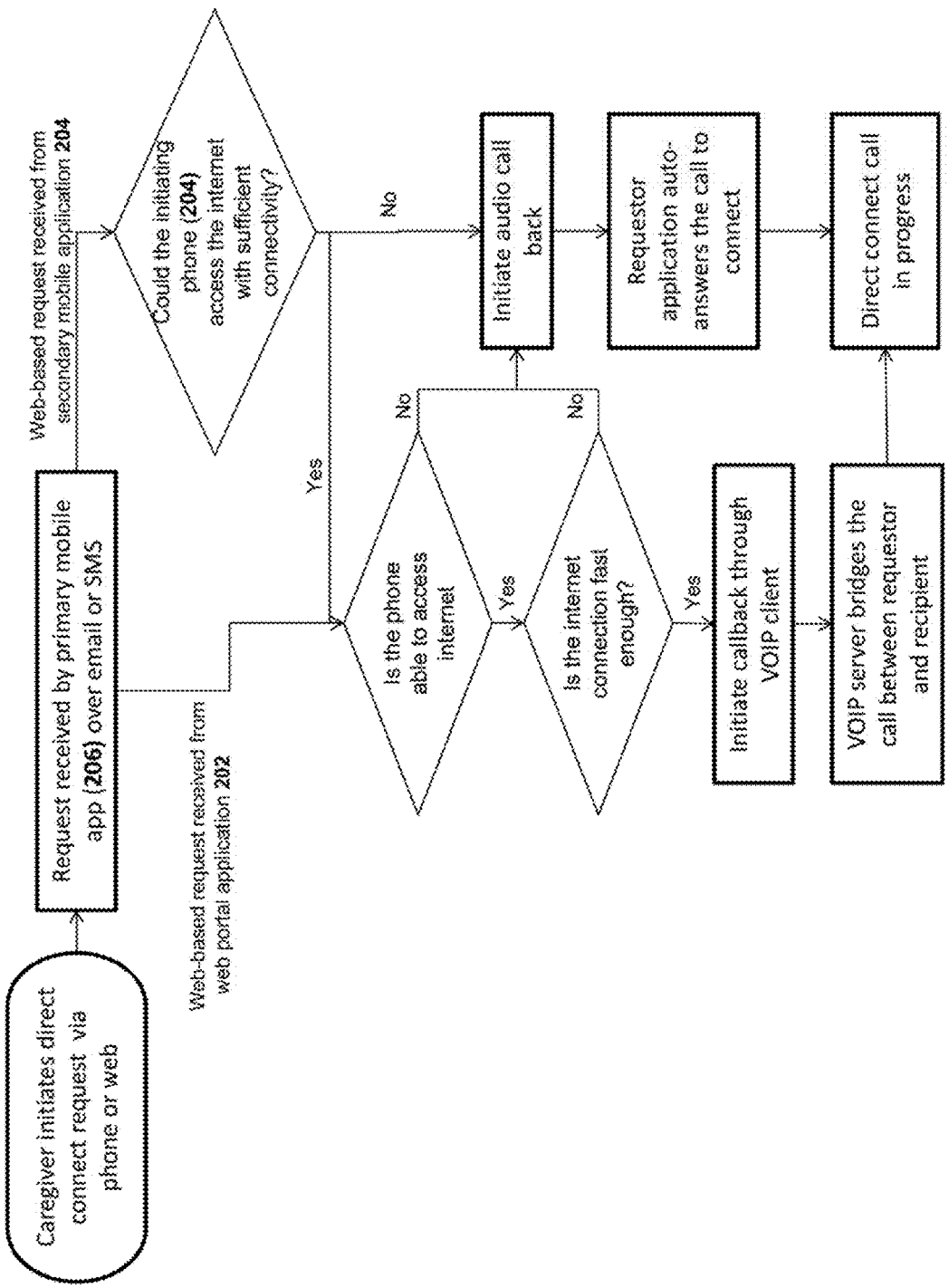
FIG. 16: *Direct Connect — Page 1*

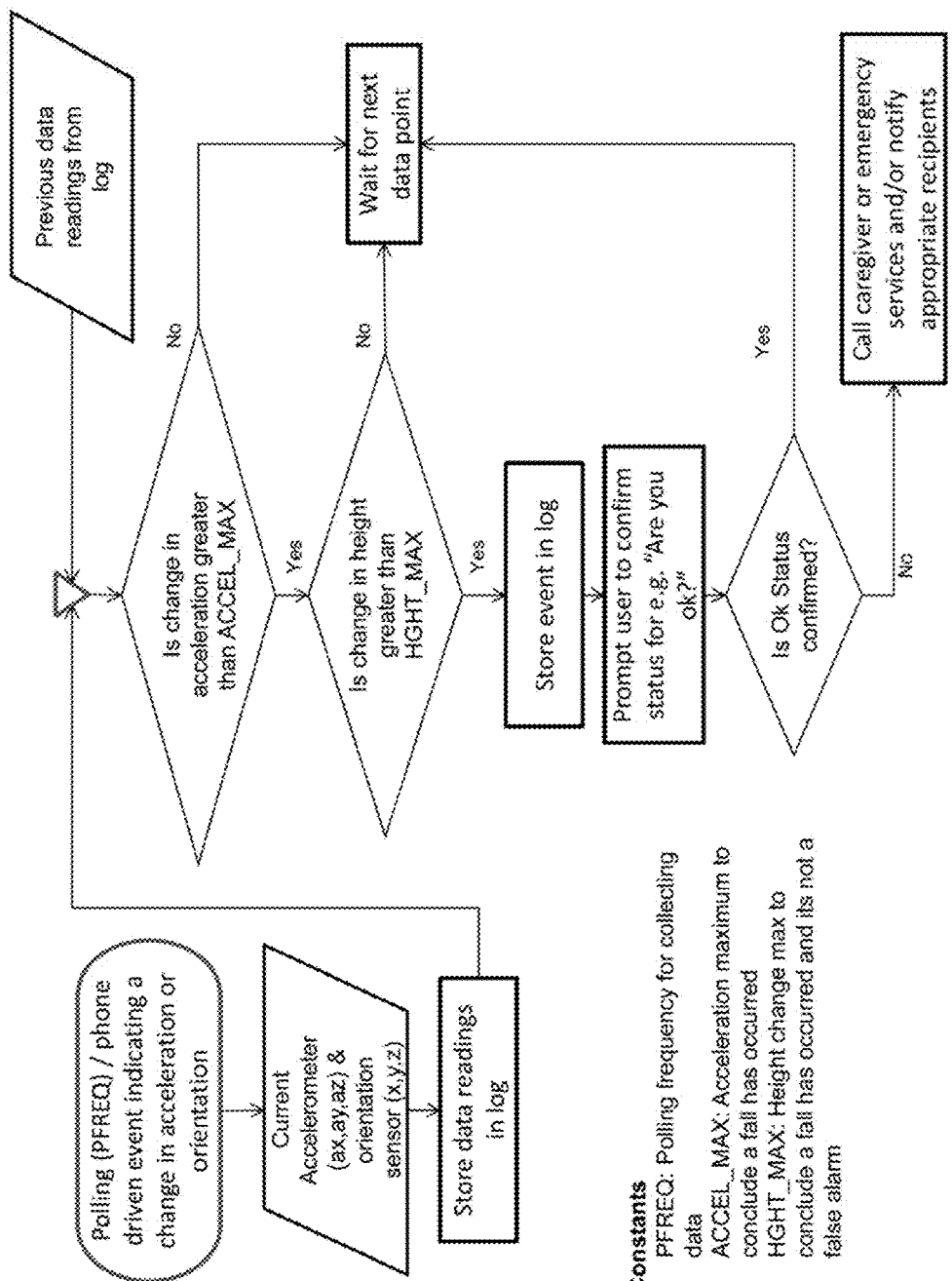
FIG. 17: *Monitoring example:* Fall detection

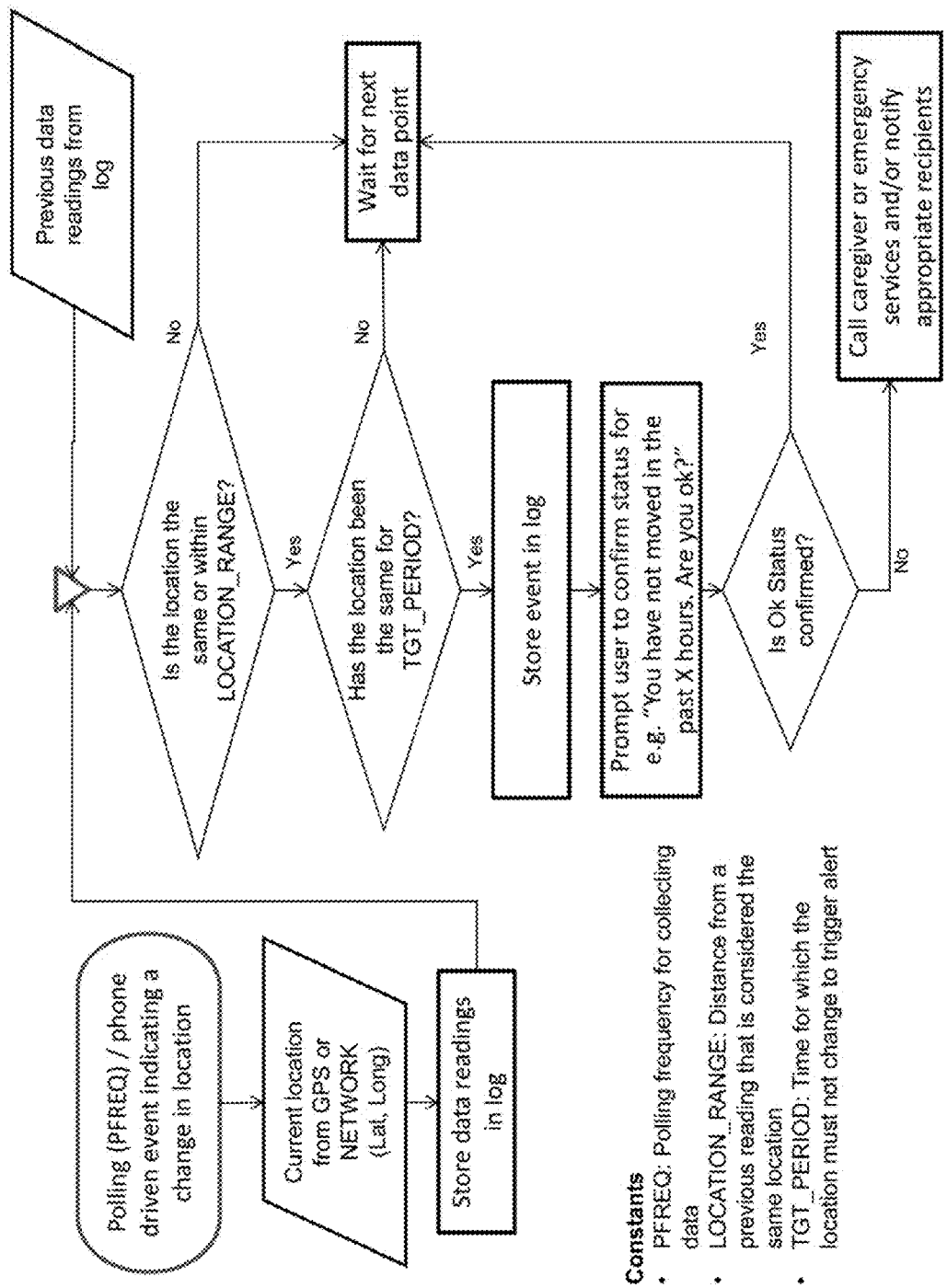
FIG. 18: *Monitoring example:* Idle check

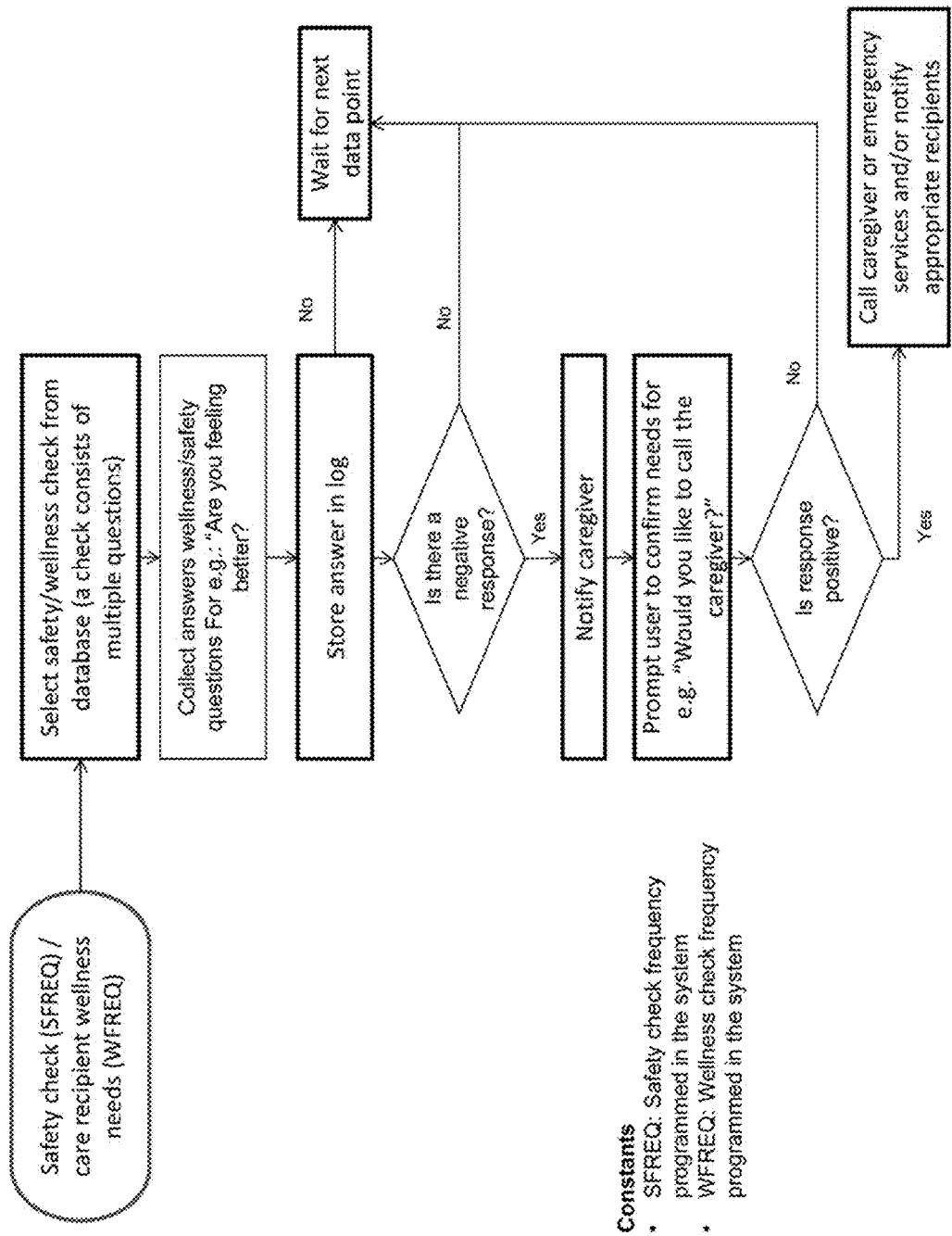
FIG. 19: Safety/Wellness check

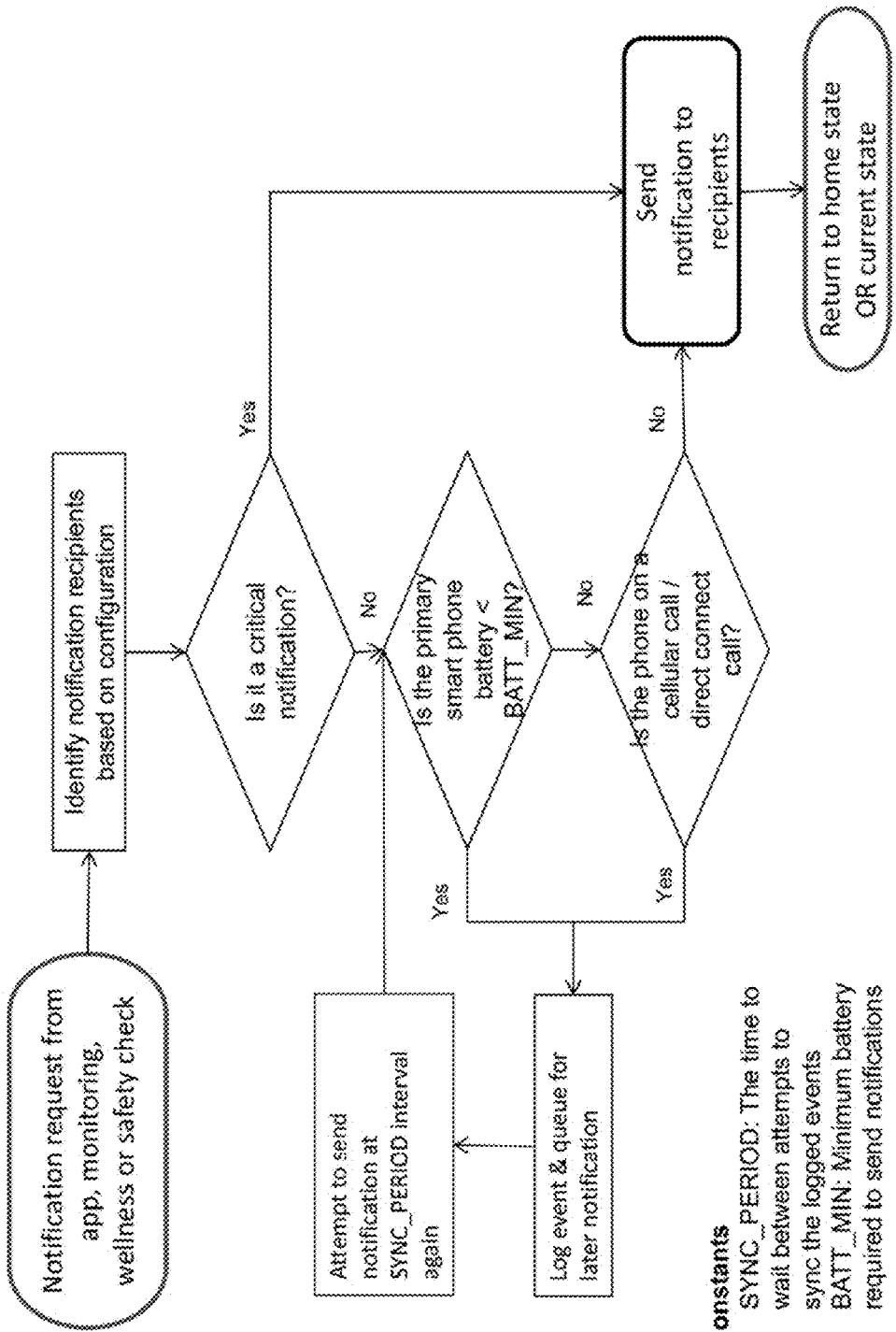
FIG. 20: Notification flow

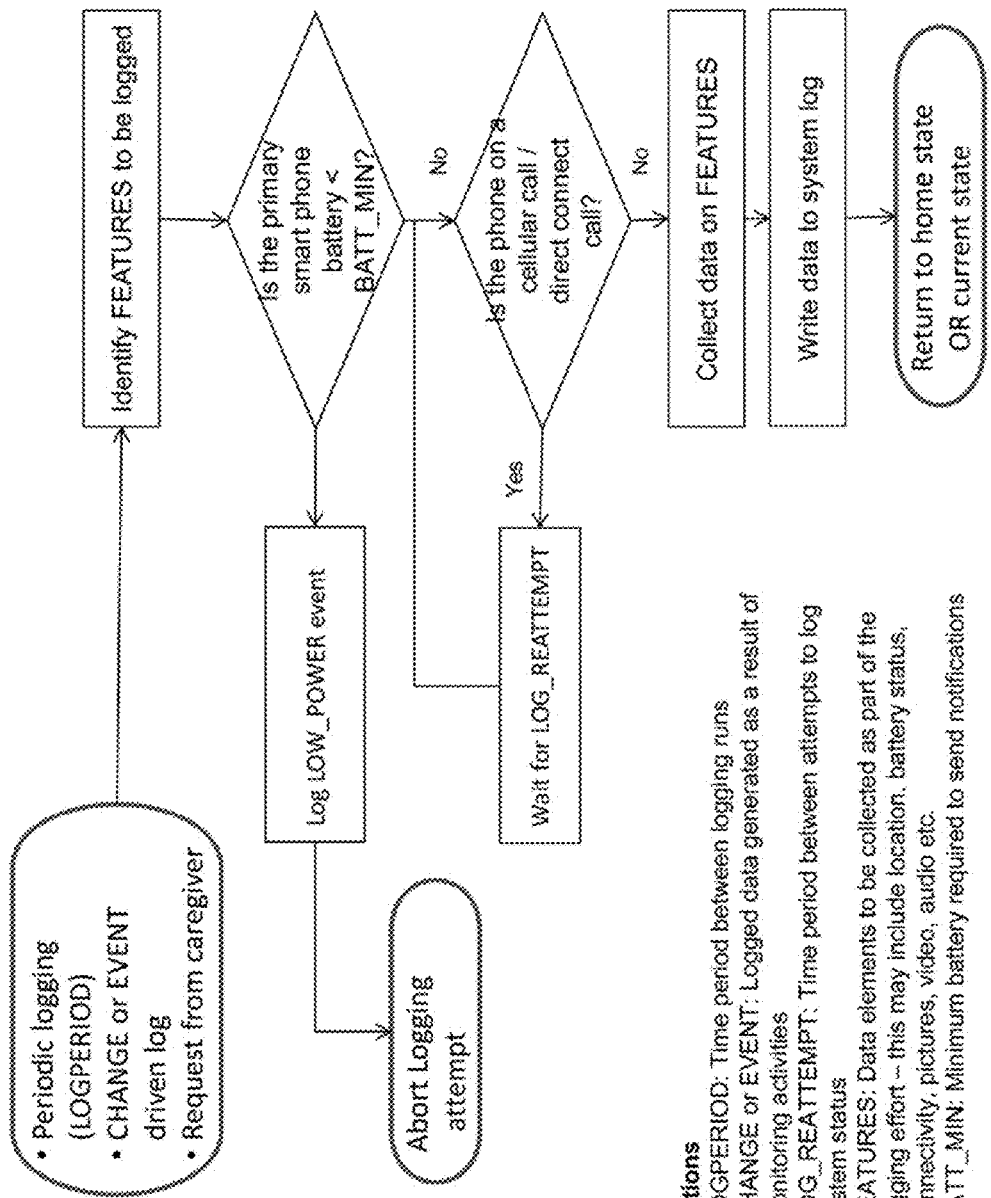
FIG. 21: Logging

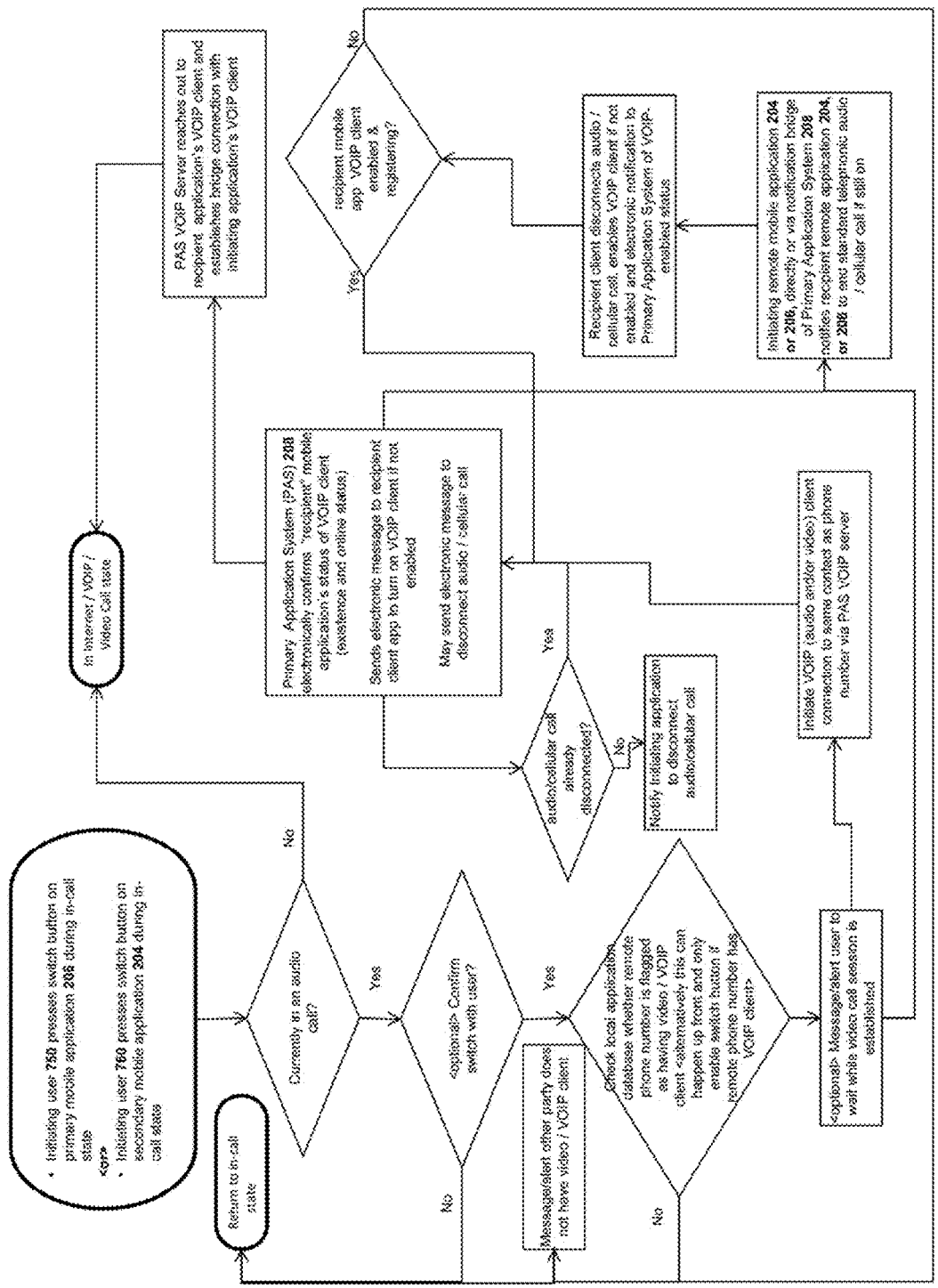

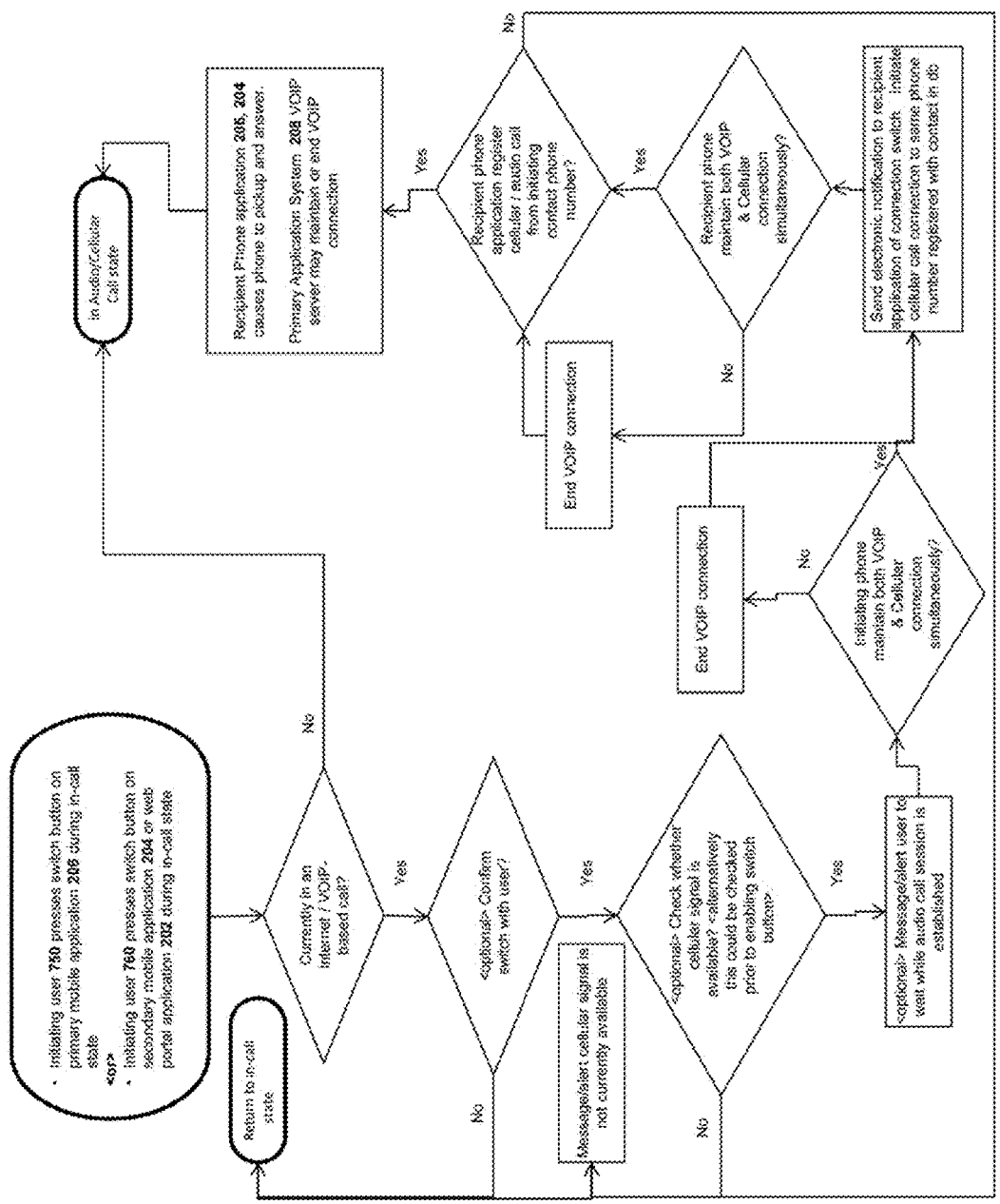
FIG. 22b: Internet / VOIP to Audio/Cellular Call Switching

SYSTEM AND METHOD FOR REMOTE CARE AND MONITORING USING A MOBILE DEVICE

CROSS-REFERENCE TO RELATED APPLICATION

This application claims benefit of U.S. Provisional Patent Application Ser. No. 61/533,600 filed on Sep. 12, 2011, the disclosure of which is incorporated herein by reference.

BACKGROUND OF THE INVENTION

The present invention relates generally to remote care and monitoring and, more particularly, to a system and method for remote care and monitoring of the user of a mobile device, such as a smartphone, and for simplifying use of the mobile device by the user.

This invention provides a unique software solution and method for facilitating the use of a mobile smartphone device while also enabling authorized users (e.g. care providers, concerned family members) to remotely interact with the mobile user, provide them medical care information, daily care instruction, alerts and reminders, general assistance, immediately connect to the mobile user's phone without them answering, provide the authorized users remote mobile phone control and tracking functions as well as remotely updating and maintaining the mobile user's mobile device.

Mobile phones historically developed for use by elderly, children or special needs groups have consisted of traditional push button cell phones modified in certain ways—via some combination of a simplified digital menu, amplified speaker, enlarged and/or paired down buttons and sometimes the addition of an urgent call and/or specialized operator button. The use of GPS or other locating device technologies has also been incorporated into some of these traditional phones for informational or emergency location purposes.

These traditional mobile phones, however, have not had the capabilities to facilitate a higher level of interaction between a mobile user and their care provider(s). While some have had features for remotely updating contact information, sending text messages or having an operator assist with dialing, there are many features and capabilities that these telephones do not have. For example, these traditional mobile phones do not have the following capabilities:

a. Allow for remotely initiating and creating a live phone (cellular) and/or Internet connection to a primary mobile phone where the primary mobile phone user does not actively answer the phone, click any button, or initiate any other kind of activity in order to do the following:
   i. Remotely enable the mobile phone's speakerphone, turn up the speaker volume and turn on the microphone in order to hear and speak with whoever or whatever is near the mobile phone itself from a secure Internet application and/or a secondary phone (land or mobile).
   ii. Remotely turn on the mobile phone's camera, automatically snap pictures and/or videos, and send them via cellular network and/or Internet using Internet upload, email or text methods to an authorized Internet site and/or specified mobile phone(s).
   iii. Remotely turn on the mobile phone's video conferencing and connect over cellular network or Internet with an authorized user via an Internet portal or specified secondary mobile phone(s).
   iv. Remotely turn on the mobile phone's location capabilities (GPS and cellular-network-based location positioning) and send those coordinates via Internet and/or cellular network using Internet upload, email or text methods to an authorized Internet site and/or specified mobile phone(s).

b. Periodically and/or through a series of predetermined times and/or via a pre-determined trigger(s) (such as those described in the instant application) automatically turn on the mobile phone's location positioning features (e.g., such as GPS, multilateration of radio signals, and/or other mobile positioning technologies) if location positioning features are off, then log the phone's location position along with a date/time stamp, possibly automatically snap picture(s) and/or video(s) (where it could be accessed on the phone) and send all that data/information via Internet or cellular connection to another user via an Internet site, email or text.

c. Automatically send a notification (call, electronic and/or otherwise) to 911, an urgent call center and/or authorized care providers and/or an Internet site if the phone is dropped, has not been moved or moved from a geographical location in a predetermined time, if the mobile user has not "checked in" by pressing a special button on the phone, by not satisfactorily answering a wellness check or mobile medical survey on the mobile phone and/or by pressing a button on a separate wireless device linked/connected with that mobile phone.

d. Automatically notify authorized users (care providers) and/or Internet site if calls are made to a predetermined list of phone number(s). For example, automatically notify (via call, electronic message or otherwise) when the mobile user's doctors, nurses, therapists, etc. are called—and then log and/or send that information with date/time stamp via Internet and/or cellular network using email, SMS, Internet upload or other electronic connectivity.

e. Automatically third party conference in pre-determined authorized user(s)/care provider(s) when calls are made to specific, predetermined phone number(s) using telephonic and/or Internet connectivity.

f. Connect wirelessly to a Personal Emergency Response System.

g. Automatically call the mobile user and/or create specialized rings/and or audio notification for when the phone battery is low and requires plugging in and/or if there is no cellular signal and also automatically notify predetermined authorized user(s) and/or Internet site of the low battery.

h. Maintain mobile user's medical profile and/or other key care information on the phone for use by physicians, nurses, therapists, emergency personnel or other medical providers. This information can be accessed and maintained locally on the phone and/or remotely via a cellular network, Internet or other electronic remote connection.

i. Maintain an automated medication alarm & schedule that can be updated remotely by an authorized user/care provider via electronic connection.

j. Allow the user to request medication refills via the mobile device that automatically send a request to the user's corresponding physician.

k. Allow an authorized user/care provider to locally and remotely maintain the mobile user's phone calendar/alarm with appointment information, date & times.

l. Allow others to send the mobile user information from a file such as Microsoft Word, Adobe Acrobat or web file (HTML-based) or a variety of image files.

m. Allow an authorized user/care provider to create custom "quick texts" for the mobile phone that allow the mobile user to text message people/contacts/phone numbers without having to type out the text messages themselves.
n. Allow an authorized user/care provider to create custom, automated wellness checks or surveys that the user responds to once or periodically and which can have custom actions associated with particular responses and/or results based on software customization. Examples of particular automated actions by the software would be electronic notification to authorized caregivers and/or notification to urgent response center and/or 911.
o. Allow an authorized user/care provider to view the message logs of the mobile phone (such as text messages, calendar and alarm notifications, and other notifications, including those automatically created).
p. Allow an authorized user/care provider to turn on and off different functions and features on the phone remotely via Internet or their own mobile phone.
q. Create hot-button dialers for different operators, concierge service, urgent care or other service providers.
r. Create a platform by which other medical/lifestyle/other application providers can interact with the mobile phone.
s. Provide a navigational interface on the phone that interacts with the user to facilitate cellular phone navigation, including hiding and/or turning on and off certain features and buttons;
t. Allow for voice-recognition-based dialing and phone navigation.
u. Alter visual and audio notifications to align with user's needs.
v. Customize the level of sophistication/complexity of the interface itself, including menu options available, applications available on the phone, ring settings and visual settings—on the phone itself and/or remotely by an authorized person.

The introduction of smartphones—mobile phones offering PC-like capabilities with technologies such as contextually changing touch screens, email, Internet browsing, Wi-Fi, GPS, an accelerometer, a magnetometer/compass, a graphical user interface operating system, a camera and the capability to run a variety of software applications—offer this potential. However, smartphones are generally feature-heavy and complicated to use, even with the most basic configurations. While these smartphones may have some of the technology capabilities mentioned available—such as software that provides location alerts or determines phone location—or the capabilities to provide the features mentioned above, the complexity and general feature-rich design of the smartphone has made it difficult for elderly, young children or people with special needs to adopt.

What is needed, therefore, is a system and method that can provide the aforementioned functionality through smartphone technology. The present invention satisfies this need.

SUMMARY OF THE INVENTION

The present invention comprises a system and method for remote care and monitoring of the user of a mobile device, such as a smartphone, and for simplifying use of the mobile device by the user. As used herein, a "smartphone" or "mobile device" should be construed to include a smartphone (sometimes referred to herein as a "mobile phone" or a "primary" mobile phone or device), a mobile tablet, and other similar portable computing devices which are able to communicate electronically (through means of cellular, wireless and/or radio communication) for which the invention could be deployed.

In the disclosed embodiment, the system and method of the present invention comprises several components, including software operable on the mobile device and/or a remote device (such as another smartphone, a computer (including, for example, a web-based application system) or other device, sometimes referred to herein as a "secondary" device). More specifically, the present invention comprises:

a. A system and method comprising software, operable on a mobile device, such as a smartphone, that, in part, simplifies the use of a smartphone by acting as an interface between the user and the smartphone features and functions. The software runs on a smartphone's operating system and behaves as a new interface to the end user, altering the phone's user interface, creating new navigation features and hiding access to other features and functions.
  i. The interface and its functions can be customized on the mobile phone itself or remotely via cellular and/or Internet connectivity by authorized users/caregivers. Examples include but are not limited to:
    1. Creating a larger dial-pad via larger graphics on the touchscreen.
    2. Simplifying menu items available and providing the ability to turn on and off functions not helpful or too complex to the end user.
    3. Turning on and off specialized functions that are helpful to the end user and may specifically assist with the user's medical or lifestyle care.
    4. Enabling a variety of audible and visual ringing/notification and interface options.
    5. Automatically calling the mobile user and/or creating specialized rings and/or audio notification for when the phone battery is low and requires plugging in and/or if there is no cellular signal. The system and method will also automatically notify authorized users/caregivers when such instances occur, including detailing a log of the situation with location coordinates and date/time stamp.
    6. Allowing for the creation of graphical emergency/urgent call buttons that provide immediate connection to an operator, 911 and/or urgent care response centers.
    7. Allowing for voice-recognition-based dialing and phone navigation.
    8. Allowing for a simpler interface to read and navigate custom news, Internet information and other messages.
b. A system and method comprising smartphone connectivity application software, operable on the remote device, that interacts with the smartphone remotely in order to remotely customize the interface software as well as to provide many of the functions and features described in the instant patent application.
c. A system and method comprising software, operable on the mobile device and/or the remote device, to remotely initiate and create a live phone (cellular) and/or Internet connection to a primary mobile phone when the primary mobile phone user does not actively answer the phone, click any button, or initiate any other kind of activity in order to do any combination or all of the following:
  i. Remotely enable the mobile phone's speakerphone, turn up the speaker volume and turn on the microphone in order to hear and speak with whoever or whatever is near the mobile phone itself from a secure Internet application and/or a secondary phone (land or mobile).

ii. Remotely turn on the mobile phone's camera, automatically snap pictures and/or videos, and send them via cellular network and/or Internet using Internet upload, email or text methods to an authorized Internet site and/or specified mobile phone(s).

iii. Remotely turn on the mobile phone's video conferencing and connect over cellular network or Internet with an authorized user via an Internet portal or specified secondary mobile phone(s).

iv. Remotely turn on the mobile phone's location capabilities (GPS and cellular-network-based location positioning) and send those coordinates via Internet and/or cellular network using Internet upload, email or text methods to an authorized Internet site and/or specified mobile phone(s).

d. A system and method comprising software, operable on the mobile device and/or the remote device, to establish cellular and Internet connectivity to a mobile phone automatically and/or remotely when that mobile device has been idle, not having had a cellular and/or Internet connection for some period.

e. A system and method comprising software, operable on the mobile device and/or the remote device, to periodically and/or through a series of predetermined times and/or via a pre-determined trigger(s) (such as those described in the instant application) automatically turn on the mobile phone's location positioning features (e.g., such as GPS, multilateration of radio signals, and/or other mobile positioning technologies) if location positioning features are off, then log the phone's location position with a date/time stamp, possibly automatically snap picture(s) and/or video(s) and send all that linked data/information via Internet, cellular or other remote electronic connection to another user via an Internet website, an email, text message and/or other form of electronic message.

f. A system and method comprising software, operable on the mobile device and/or the remote device, to automatically send a notification (in the form of a call, electronic and/or otherwise) to 911, an urgent call center and/or authorized care providers and/or an Internet site if the mobile phone is dropped, has not been moved or moved from a geographical location for a predetermined amount of time, if the mobile user has not "checked in" by pressing a special button on the phone, by not satisfactorily answering a wellness check or mobile medical survey on the mobile phone and/or by pressing a button on a separate wireless device linked/connected with that mobile phone.

g. A system and method comprising software, operable on the mobile device and/or the remote device, to automatically notify specified users (e.g., care providers) and/or an Internet site if calls are made to a predetermined list of phone number(s). For example, automatically notify (via call, electronic message or otherwise) when the mobile user's doctors, nurses, therapists, etc. are called—and then log and/or send that information with date/time stamp via Internet and/or cellular network using email, SMS (short message service), Internet upload or other electronic connectivity.

h. A system and method comprising software, operable on the mobile device and/or the remote device, to automatically party conference a mobile phone with pre-determined specified user(s)/care provider(s) via telephonic and or Internet connectivity when calls are made to specific, predetermined phone number(s).

i. A system and method comprising software, operable on the mobile device and/or the remote device, to allow an authorized user/care provider to create custom, automated wellness checks or surveys that the mobile user responds to once or periodically and which can have custom actions associated with particular responses and/or results based on software customization. Examples of particular automated actions by the software include without limitation electronic notification to authorized caregivers and/or notification to urgent response center and/or 911 containing or providing access to survey results, medical or other information, including software-triggered recommendations, mobile phone location tracking information, pictures, audio and/or video captured from the mobile phone.

j. A system and method comprising software, operable on the mobile device and/or the remote device, for providing caregiving features to a user through a mobile smartphone and/or remote Internet-based application, including without limitation the features discussed above and the following additional features:

i. Medically-related instructions including therapy and medication instructions sent to mobile user by authorized remote user/caregiver or authorized medical provider ii. Specialized alarms, alerts and schedules that notify the user of appointments and provide related, relevant information. For example, a doctor appointment reminder that also includes instructions on diet and driving directions linked together and then logged on the mobile phone and via Internet with date/time stamp, the type of alert or alarm, the information linked with alarm and the mobile user's response (such as acknowledgement of the alarm). These alarms, alerts & schedules could also be linked with actions that the mobile user can take—such as responding with text communication or phone call to relevant parties to the alarm or automatically refilling medication. These alarms, alerts and schedules can be setup on the mobile phone itself or remotely through a cellular and/or Internet connection by an authorized user/caregiver.

iii. Medication tracking features that notify user when the time for a refill is approaching and whether a refill is available. The system and method can automatically request a refill and/or renewal on medications or can prompt the mobile user to have the system and method automatically request a refill and/or renewal to the physician(s) and/or the user's choice pharmacy. The system and method also logs the events, information and associated actions for reference by an authorized user/caregiver. These medication tracking features and actions can be setup on the mobile phone itself or remotely through a cellular and/or Internet connection by an authorized user/caregiver.

iv. Specialized hot buttons dialers for initiating urgent calls to 911 and/or urgent response centers, different operators, concierge service and/or other service providers. Once pressed, these buttons not only connect user to 911 and/or urgent response centers (or other intended receiver), they also cause notification to authorized users/ caregiver(s) and a logging of event for view by and notification to authorized users/caregiver(s). These button(s) can be graphical action buttons on the mobile phone screen or buttons located outside the screen on the mobile phone itself v. A series of pre-customized texts that the mobile user can use to communicate to authorized users/caregivers and/or medical providers without having to type an entire or portion of a text notification. These pre-customized texts can be customized on the mobile phone or remotely by an authorized user/caregiver.

vi. Specialized Internet and mobile phone portals for administrative and caregiving access and interaction with the mobile user and among one another by a mobile user's medical providers, living facility administration, urgent response centers, other lifestyle and/or application providers and authorized caregivers.

k. A radio alert connectivity device that, when activated, sends a signal to its host radio-enabled mobile phone (ex. via Bluetooth) to dial a predetermined number and/or connect via secure Internet connection to a predetermined application (call center or authorized user). The alert connectivity device also contains a microphone and speakerphone that can be used to listen and speak with the person/call center to which the phone connected. The device also initiates location tracking of the smartphone device, message notifications (via text, email or Internet) to authorized third parties and picture capture & send. This functionality essentially turns phone into a mobile Personal Emergency Response System (PERS).

l. A system and method comprising software, operable on the mobile device and/or the remote device, for remotely customizing mobile phone—including font size, screen colors, volume, creating and setting custom alarms with calling actions, creating and setting custom surveys with calling actions, editing/updating phone contact information, medical profile, turning on/off certain features as well as interacting via the various methods and features discussed herein.

m. A system and method comprising software, operable on the mobile device and/or the remote device, for maintaining a medical profile of the mobile user on the mobile phone that can be accessed and/or updated on the mobile phone itself or remotely via cellular and/or Internet connection by authorized users.

n. A system and method comprising software, operable on the mobile device and/or the remote device, for identifying a shaking pattern and/or voice recognition process that results in the mobile phone answering the phone and/or taking other pre-determined actions (instead of pushing a button to answer the phone or take an action).

o. A system and method comprising software, operable on the mobile device and/or the remote device, to provide the aggregated feature set or subsets of the capabilities and features described herein, for use in connecting users and caregivers with elderly and/or children and/or special needs for urgent and non-urgent situations. The feature set includes without limitation direct connect, automated remote connectivity, location tracking, automated picture sending/remote camera monitoring, automated fall detection, automated wellness checks/custom actionable surveys, remotely updating and customizing mobile phone from secure Internet application/mobile applications).

p. A unique purchase and installation process.

These and other features and advantages of the present invention will be apparent from the following detailed description, in conjunction with the appended claims.

BRIEF DESCRIPTION OF THE DRAWINGS

The benefits and advantages of the present invention will become more readily apparent to those of ordinary skill in the relevant art after reviewing the following detailed description and accompanying drawings, wherein:

FIG. 15 is a flowchart illustrating the overall operation of the primary smartphone application in accordance with the principles of the system and method of the present invention;

FIG. 16 is a flowchart illustrating the process by which a direct connect call may be initiated in accordance with the principles of the system and method of the present invention;

FIG. 17 is a flowchart illustrating the monitoring process for determining whether the user/primary smart phone device has fallen in accordance with the principles of the system and method of the present invention;

FIG. 18 is a flowchart illustrating the monitoring process for assessing and evaluating a potential "idleness" event and follow-up actions as a result in accordance with the principles of the system and method of the present invention;

FIG. 19 is a flowchart illustrating the process followed to execute, collect and log answers for a safety or wellness check in accordance with the principles of the system and method of the present invention;

FIG. 20 is a flowchart illustrating the notification process flow for dispensing notifications in accordance with the principles of the system and method of the present invention;

FIG. 21 is a flowchart illustrating the logging process in accordance with the principles of the system and method of the present invention;

FIG. 22a is a flowchart illustrating the process for switching from a standard telephonic, cellular-based audio phone call to an Internet-based, VOIP connection that allows both audio and/or video connectivity while a standard, telephonic, cellular-based audio phone call is underway within the application system in accordance with the principles of the system and method of the present invention; and, FIG. 22b is a flowchart illustrating the process of switching from an Internet-based/VOIP connection to a standard telephonic, cellular-based audio phone call while an Internet-based/VOIP connection is underway within the application system in accordance with the principles of the system and method of the present invention.

DETAILED DESCRIPTION OF THE INVENTION

Figure 1:
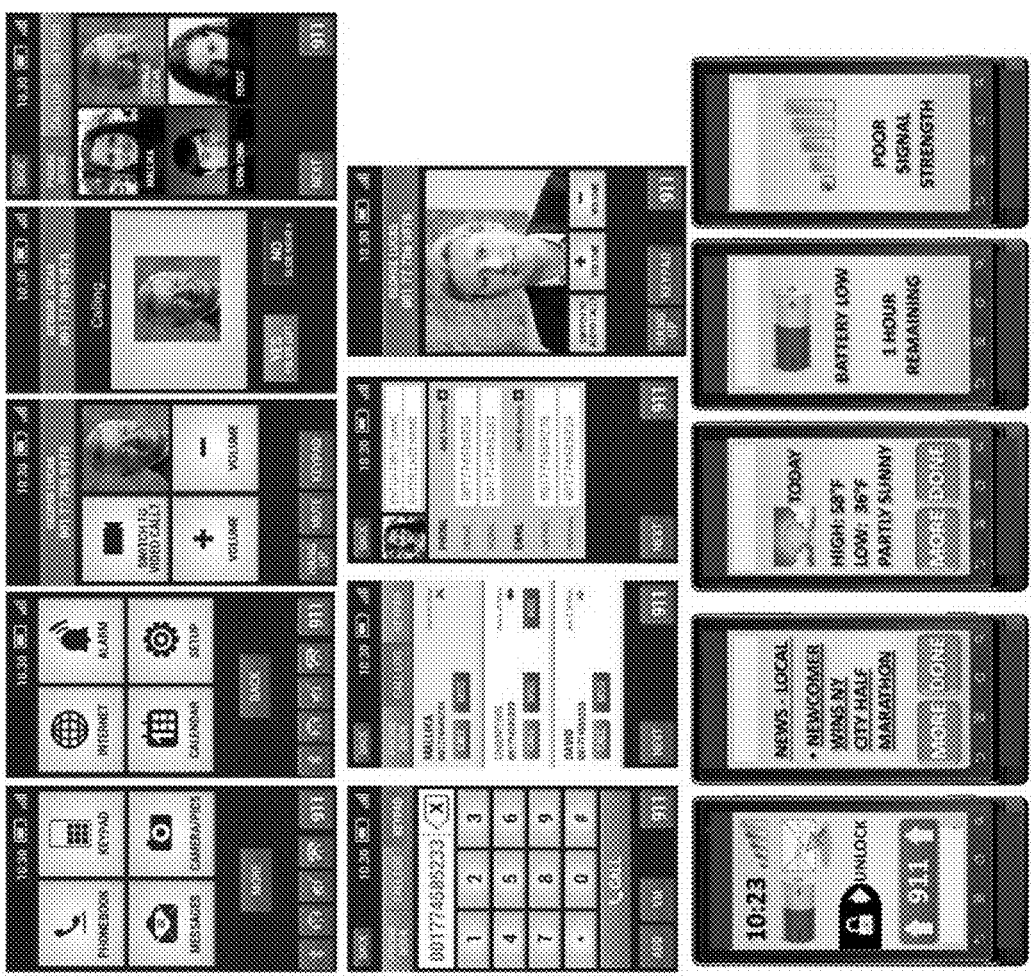
FIG. 1 is a series of screen shots illustrating exemplary interfaces in accordance with the principles of the system and method of the present invention.

The benefits and advantages of the present invention will become more readily apparent to those of ordinary skill in the relevant art after reviewing the following detailed description and accompanying drawings.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification does not imply, nor should be inferred to limit, the subject matter disclosed herein.

In a disclosed embodiment, the system and method of the present invention comprises the individual and aggregated feature set and/or subsets of the capabilities and features described in the instant application, for use in connecting primary users 750 and authorized remote parties 760 (e.g., caregivers) with one another for urgent and non-urgent situations.

The feature set includes but is not limited to audio and/or video direct connect, automated remote connectivity, automated call conferencing based on predetermined phone numbers, location tracking, automated picture and/or video sending/remote camera monitoring, automated location tracking with photo and/or video logging, intelligent monitoring of urgent and non-urgent situations, including but not limited to lack of movement with the primary mobile phone 206, lack of reaching a location by the primary mobile phone 206, automated fall detection, automated wellness checks/custom actionable surveys, as well as remotely updating and customizing the primary mobile phone 206 application (it will be appreciated that reference numeral 206 refers to the primary mobile phone with software installed thereon, sometimes referred to herein as the "application," for causing the primary mobile phone to operate in accordance with the principles of the system and method of the present invention) in from a secure Internet application 202 and/or secondary mobile applications 204 and a specialized user interface that compels the primary application user 750 to utilize their phone 206 though it is not required to make use of the application features described herein.

The system and method of the present invention is designed, in part, to interact with some of the innate programmed features of the mobile phone but mask the phone's standard user interface and navigation so that those innate features (such as the dialer, the user phone book, the web browser, the camera, battery indicator, and menu options) are accessible to the user in a simplified, easier-to-use interface presented to the primary mobile application user. Developing an interface that overlays an existing interface is a well-documented process and is known to those skilled in the art. It is accomplished through basic level application programming interface (API) and/or other coding utilized by the manufacturer and/or operating system provider of the smartphone to connect and interact with the phone's hardware and operating system features.

The application interface is built through a series of screens that contain a combination of buttons, text information, graphics and/or interactive objects that are part of the interface API functions of a smartphone. Examples of interactive objects include virtual graphic buttons, physical buttons that are part of the phone itself, text boxes, selection lists, radio buttons, check boxes and other objects as are known to those skilled in the art. Interactive objects leverage user feedback in order to take action and are generally part of the smartphone's operating system API. The inclusion of the interface as a part of the instant invention is necessary not for the novelty of creating an interface but for the novelty of the interface itself and also for the novelty in how the interface is being applied to the utilization of the various embodiments of the invention described herein.

It will be appreciated by those skilled in the art that the system and method of the instant invention may be adapted to operate with any number of mobile device operating systems (including without limitation iOS, Android, etc.), mobile devices (including without limitation iPhones, iPads, etc.) and desktop operating systems (Mac OS, Windows, etc.). All such mobile operating systems, devices and desktop operating systems are included with the scope of the instant disclosure.

As seen in FIG. 1, the system and method of the present invention provides a simplified mobile device interface. The exemplary interfaces illustrate simplified mobile device navigation and provide:

A simple, uncluttered design

Large, easy-to-read, high-contrast text and buttons

Intuitive to use, haptic (sensory) feedback that simulates pressing of buttons

Loud, flashing ring tones

Voice recognition dialing and navigation integrated

Video conference capabilities where available

Clear, easy to read and understand instructions

A simplified way to read news and information

Some of the novel features of the interface, also shown in FIG. 1. include:

- Phonebook and other configurable features of the phone and of the primary mobile application 206 described can be remotely updated by an authorized user 760 such as a caregiver or service operator
- An alert in the form of a pretend phone call that mimics a real call by alerting the primary mobile user 750 with a telephone ring and then prompting user 750 audibly and visually that the battery is low and/or that they are out of cell range
- Physical shaking of phone to prompt phone to ask primary mobile user 750 if they intend to dial 911 or other urgent call center and then do so upon user 750 confirmation
- Allowing the primary mobile user 750 to make VOIP calls directly from the application 206 and/or to switch back-and-forth between standard telephonic, cellular-based audio phone connectivity and/or a VOIP audio connectivity and a VOIP/Internet-based audio and video connection via the interface, including while a phone call is underway in the application system or a while a phone call may appear to be underway in the application system.
- Allowing the primary mobile application user 750 to switch among prebuilt interface designs to accommodate their needs or preferences around font size, color contrast, sound and volume features.
- Allowing the primary mobile user 750 to access features of the primary mobile application 206 described in detail in the instant application, including, but not limited to:
  - Ability to receive and respond to primary mobile application alerts, status check-ins that are launched by the application, mobile wellness checks, medication and other reminders, electronic messages; these alerts are not simply calendar alerts but also have actionable response options such as allowing the user to alter prescription information on the user's medical profile of the primary mobile application 206
  - Configuring the primary mobile application itself, including enabling and/or disabling certain application features such as direct connect, fall detections, electronic PERS radio receiver connectivity, configuring authorized remote users such as caregivers, wellness checks and/or any of the other primary application configuration options described herein.
- Allowing the primary mobile user to press a button that launches the secondary mobile application 204 (it will be appreciated that reference numeral 204 refers to the secondary mobile phone or device with software installed thereon, sometimes referred to herein as the "application," for causing the secondary mobile phone or device to operate in accordance with the principles of the system and method of the present invention) of the invention described here and/or integrates the features of the secondary mobile application 204 described herein.

The details for the novel implementation of the collection of these features are further discussed in the instant application. For those comfortable with navigating a modern smartphone, the interface of the primary smartphone application 206 can be customized to hide and/or to turn on and off other applications, phone features and buttons (such as the search button, home button, or the camera or web browser). The software of the system and method of the present invention can run in the background to provide the powerful caregiving connectivity features that assist with both resolving urgent situations and enhancing daily interactions even if the simplified interface is turned off.

If the interface is turned on, it helps facilitate the navigation and use of the monitoring and caregiving features described herein through direct access to many of those features and the configuration of those features. Furthermore, many of those would-be primary mobile application users are not able and/or willing to use the smartphone in its native form because of any combination of issues, such as: over complexity of the phone including features and functions that are foreign and wouldn't be utilized by the user; small or difficult to read fonts and font size; lack of enough contrast among graphics and text that make it difficult to see and/or read; difficulty configuring the phone with the functions desired; difficulty navigating the phone because of concepts and features not found in traditional phones; etc.

With the primary mobile application 206 interface, many of these users would now be able to successfully use a smartphone to make calls and then leverage the smartphone to interact with loved ones and caregivers because the interface provides an easy, intuitive way for them to use a smartphone and a direct, easy and intuitive way to perform the many helpful caregiving functions of the primary mobile application 206 described in this document. If enabled, the primary mobile application interface will run as soon as the smartphone itself is booted up as part of the start sequence in order to mask other smart phone functions via the interface.

The primary mobile application 206 functions by resting in a home state and then being triggered to change states based on a variety of internal and/or external triggers. The application 206 then takes action in those different states, sometimes switching among the states, until completing the series of tasks and returning to the home state configuration.

FIG. 15 illustrates the core process functioning of the primary mobile application 206 by detailing some of the major different states and state changes that the phone goes through when the primary smartphone application 206 (with or without the interface enabled) is running.

The home state is the default starting point for the system. In the home state, the application displays a simplified interface for the user 750 to interact with the primary smartphone 206 unless the user has turned off the interface as described above. If the interface is disabled, the user 750 interacts with the mobile phone operating system regularly while the primary application core activities run in the background. The smartphone's 206 operating system API allows users to create activities/processes and have them run in the background. Either way (interface enabled or disabled), in the home state, some core activities run in the background, idle until they are triggered. Examples include: (a) logging, (b) fall detection, (c) idleness checks, (d) wellness/safety checks, (e) other monitoring and notification functions, and (f) direct connect receiver that are described herein.

These background activities of the primary mobile application system 206, each described briefly below and then in further detail later in the instant application, may or may not prompt user interaction at different points. When invoked, these background activities may change the state of the phone to require an interaction either from the primary mobile user 750 or remotely from an authorized remote user 760.

The states displayed in FIG. 15 and shown below illustrate a sampling of changes from the home state that may prompt a user interaction:

a. Monitoring notifications: The primary mobile application 206 will display monitoring-related notifications to users 750 to acknowledge. These are asynchronous, and may pop-up any time a monitoring process 650 indicates an event. Monitoring tasks run in the background, unless user input is required per Notification Triggers 802.

Examples include, but are not limited to: monitoring for a phone shake which prompts the user if they want to dial 911 or other urgent facility and waits for user response; monitoring to detect a fall, which when detected prompts user with a status check; monitoring phone movement through GPS (global positioning system) and accelerometer hardware for lack of movement, for not reaching a particular destination and/or to infer location destinations and/or speed of movement; monitoring responses to alarms, reminders, wellness and safety check-ins. Monitoring notifications may also prompt remote authorized user(s) 760 to be notified of primary mobile application 206/primary mobile application user 750 status and/or to login to the secondary mobile application 204 or web application interface 202 to obtain more detail and/or take some action based on notification. For example, a monitoring notification may prompt the primary mobile application user 750 to take a medication at a specified time as setup in their medical profile of the primary mobile application 206. The primary mobile user 750 can respond to the notification by clicking a button that says something to the effect of "I no longer take that medication". That response may prompt a removal in the monitoring notifications of any further similar reminders. It may also send notification to remote authorized caregiver(s) 760 indicating the primary application user 750 has indicated they no longer take the medicine and asking the remote authorized user 760 if they would like to confirm the stopping of the medication or re-enable the medication reminder and potentially alter or update it with relevant information and possibly message the primary application user 750 that they were re-enabling the reminder and the reason for it. In such a case, the primary application 206 would receive a second notification with the remote authorized user's 760 actions and message.

b. Incoming or outgoing calls including direct connect requests: The system and method of the present invention may receive or place a call (including direct connect call) requiring the switch from the home state to the call or direct connect interface. The process and methods by which a remotely authorized user 760 can initiate and create a live phone (cellular) and/or Internet audio and/or video connection to a primary mobile phone 206 where the primary mobile phone user 750 does not actively answer the phone, click any button or initiate any other kind of activity is collectively referred to herein as a "direct connect" or "direct connection."

c. Wellness & safety checks: These run at prescheduled times per the configuration. The system and method of the present invention interacts with the users to collect information on specific wellness and safety related checks. These checks may further trigger notifications to either or both the primary application user 750 and/or the remote authorized user 760. Such notifications may then prompt further monitoring processes that await further user action such as those described in monitoring notifications above.

d. Phone configuration: The user may choose to change how the primary mobile application or phone 260 is setup, changing application parameters or phone behavior. The changes to the configuration may require further synchronization, access to phone memory and notifications.

e. Logging: The system and method of the present invention logs features that may require the phone to switch out of the home state to collect data, such as camera pictures. The system and method of the present invention collects information, as appropriate and configured and then returns to the home state or current state that smartphone was in prior to logging initiation.

f. Primary mobile application user interaction: The user may choose to interact with other features of the interface and go into customized interfaces to explore content such as communities, billing, administration, getting help from the helpdesk etc.

Figure 2:
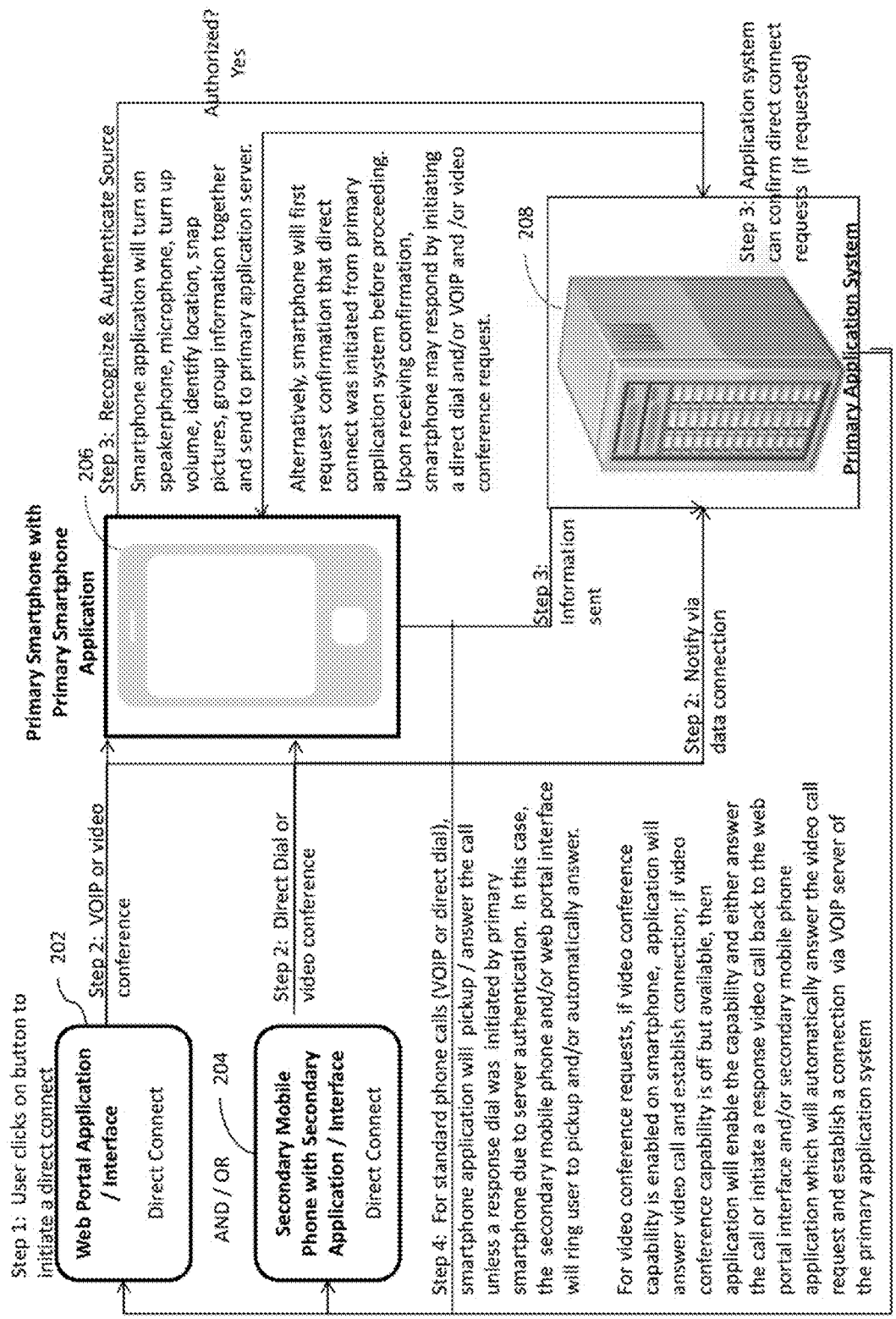
FIG. 2 is a flowchart illustrating initiation and creation of a live phone (cellular) and/or Internet connection to a primary mobile phone where the primary mobile phone user does not actively answer the phone, click any button, or initiate any other kind of activity in accordance with the principles of the system and method of the present invention.

FIG. 2 illustrates the system and method of the present invention used to remotely initiate and create a live phone (cellular) and/or Internet audio and/or video connection to a primary mobile phone 206 where the primary mobile phone user 750 does not actively answer the phone, click any button, or initiate any other kind of activity. This process may collectively be referred to herein as a "direct connect" or "direct connection."

The purpose of a direct connection is to allow an authorized remote user 760 the ability to see, hear and interact with the primary mobile application user 750 at the authorized remote user's discretion, and to connect with the primary application user 750 (which may be a care recipient) for primarily concerning, urgent or potentially urgent situations. The authorized remote user 760 might also leverage the information gathered through the monitoring processes and logged from the primary smartphone application 206 in order to help illustrate what may have transpired recently with the primary mobile application user 750.

In just one example of a direct connection in accordance with the principles of the system and method of the instant invention, the primary mobile application user 750 responds negatively to a wellness check survey from the primary mobile application 206, perhaps indicating they aren't feeling well. The primary mobile application 206 recognizes the input response as a negative response because response options are pre-configured in the primary mobile application 206 as positive, negative or neutral. The application 206 may respond to the primary application user 760 with a follow-up question based on the logic tree of the wellness check or perhaps it may recommend calling a doctor or 911. The primary user 750 may choose to take action or may choose not to call or take action.

Regardless, the primary mobile application 206 may send an electronic notification (email, SMS and/or securely through the web portal application 204 and/or the secondary mobile application 206 to inform the remote authorized user(s) 760 of wellness check outcome and subsequent activities of the primary mobile application and primary mobile phone 206 including but not limited to: any calls made; date/time-stamped history of location(s) to which the phone traveled tagged with (or without) pictures and/or video taken at those periodic intervals throughout the day; and/or any relevant urgent-or non-urgent producing notifications. The remote authorized user 760 may then have called the primary application user 750 with no response. The remote authorized user 760, having special permission in the primary mobile application 206 configuration, may then initiate a direct connect to turn on the primary authorized user's phone to try and interact with them to make sure they are alright and taking the appropriate actions.

As shown in FIG. 2, the steps for a direct connection in one embodiment of the system and method of the present invention comprise:

Step 1: Initiation

Figure 3:
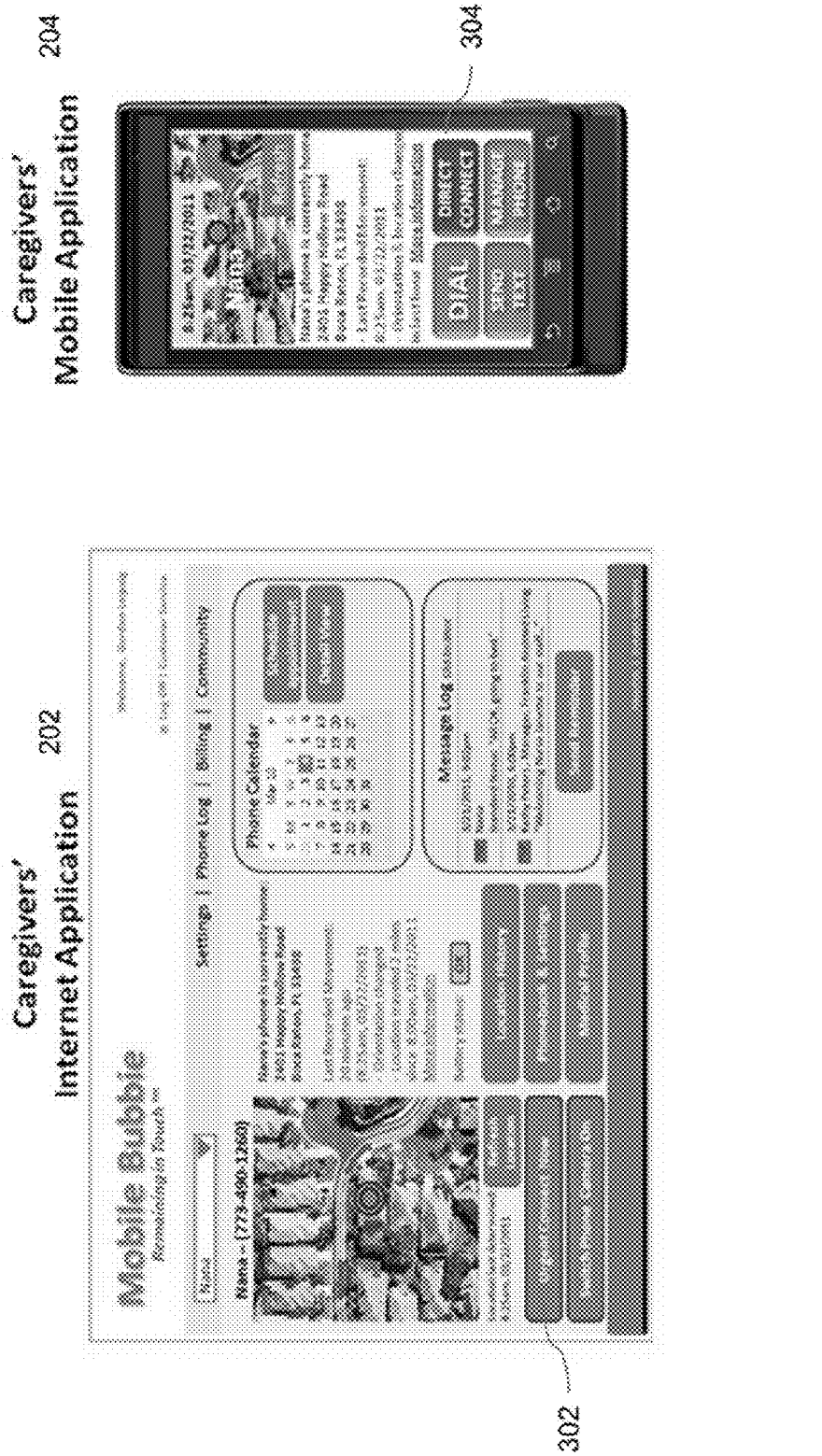
FIG. 3 is a series of screen shots illustrating exemplary "Urgent Connect Now" (on the web application) or "Direct Connect" (on the secondary mobile application) buttons/interfaces in accordance with the principles of the system and method of the present invention.

A remote authorized user 760 presses a button to initiate a direct connection from either a web application 202 or a secondary mobile phone application 204. As shown in FIG. 3, "Urgent Connect Now" 302 on the web application 202 and "Direct Connect" 304 on the secondary mobile application 204 are exemplary buttons. In one embodiment of the system and method of the present invention, the option to press the button is available only to pre-authorized users 760 whose electronic profile has been specially flagged in the primary application system 208 data store (stored on a suitable computer system) and/or communicated to the primary smartphone application 206 data store during either the application setup or configuration processes and stored in the configuration data 660 that is shared among the primary application system 208, the primary smartphone 206 and the web portal application 202 and secondary mobile phone application 204 as being allowed to initiate a direct connection.

Step 2: Notification of Direct Connect Intention

There are two alternatives for how this process may occur:

Alternative 1: Immediately Call

If the direct connection was initiated through a web-portal application interface 202, the system and method of the present invention will initiate an Internet-based Voice-Over-IP (VOIP) call, cellular call and/or hybrid VOIP-cellular call to the primary mobile smartphone 206 through the primary application system 208 or another method. If the smartphone has video conference capabilities, then the web-portal application 202 via the primary application system 208 will initiate a video conference call instead. The primary system application 208 will recognize video conference capabilities through configured settings in the primary application system 208 data store that maintain status of whether the primary smartphone 206 has the hardware and software capability for video conferencing. In one embodiment of the invention, such information is linked and stored during the setup and/or configuration process and stored in the configuration data 660 that is shared among the primary application system 208, the primary smartphone 206 and the web portal application 202 and secondary mobile phone application 204.

If the direct connect was initiated through a secondary mobile phone 204, the system and method of the present invention will directly call the primary mobile phone 206 through a cellular network, VOIP and/or hybrid VOIP-cellular call or indirectly call the primary mobile phone 206 via the primary application system 208 using cellular network, VOIP and/or hybrid VOIP-cellular call. If the system and method of the present invention both the primary smartphone 26 and the secondary mobile phone 204 have video conference capabilities, then the secondary mobile (or smartphone) application 204 will initiate a video conference call instead that may go directly to the primary mobile phone 206 or indirectly through the primary application system 208. The primary smartphone application 206 and/or the primary application system 208 will recognize video conference capabilities through configured settings in the primary application system 208 data store that maintain status of whether the primary smartphone 206 has the hardware and software capability for video conferencing.

In parallel, the clicking of the direct connect button in web portal application 202 and secondary mobile application 204 will also notify the primary application system 208 that a direct connect call is being placed as well as set specialized flags in the primary application system 208 and/or the secondary mobile application system 204 that a direct connect call is being requested.

Alternative 2: Notify the Primary Application System 208 to Request a Direct Connect The web portal application 202 and/or the secondary mobile phone application 204 of the system and method of the present invention will electronically notify the primary application system 208 that a direct connection call is being requested as well as set specialized flags in the primary application system 208 and/or the secondary mobile application system 204 that a direct connect call is being requested.

Step 3: Authentication & Validation

There are two major alternatives based on the process followed in Step 2:

Alternative 1: Incoming Calls

The primary mobile smartphone application 206 will recognize the caller or the source of the call (audio and/or video call) as it is pre-configured with authorized user 760 identifiable information and/or secondary mobile phone 204 identifiable information. The primary mobile smartphone application 206 will pick up any combination of the source phone number, source IP address, and/or other user identifiable information associated with the person initiating the direct connection as obtained by logging into the web portal application 202 and/or the secondary mobile application 204. There are two primary options based on this alternative:

Option 1: The primary mobile smartphone application 206 recognizes the source as having permission to direct connect and automatically causes the primary smartphone itself 206 to connect/pick up the direct call and/or video conference call (if video conferencing is available and enabled). If video conferencing is not enabled, then the primary mobile phone 206 may enable it and then connect or respond video conference dial to the initiating web portal 202 and/or secondary mobile phone application 204.

Option 2: The primary mobile smartphone 206 makes an electronic authorization and validation request of the primary application system 208 to ensure:

A. That the requesting source is an authorized source, and/or

B. To validate that the requesting source is not only authorized but actually requesting a direct connection (as opposed to simply requesting a "regular" call/video conference connection).

Upon authorizing and validating, the primary mobile smartphone application 206 causes the primary smartphone to pick up the call or call back the source through cellular, VOIP and/or hybrid cellular-VOIP means. If video conferencing is not enabled, then the primary mobile phone 206 may enable it and then connect or respond with video conference dial to the initiating web portal 202 and/or secondary mobile phone application 204.

Alternative 2: Incoming Request for a Direct Connect

The primary application system 208 will electronically notify the primary mobile smartphone 206 that an authorized direct connection is being requested (via a web-based/Internet application data transfer, text message, email or other electronic means).

At that point, the primary smartphone application 206 will automatically call the requesting web portal 202 user 760 and/or secondary mobile phone 204 user 760 through cellular, VOIP and/or hybrid cellular-VOIP means. If video conferencing is requested then, if it is not enabled, then the primary mobile phone 206 may enable it and then connect or respond with video conference dial to the initiating web portal 202 and/or secondary mobile phone application 204. The web portal application 202 (as linked with the primary application system 208) and/or the secondary mobile phone application 204 will have had a flag set to automatically pick up call from the primary smartphone 206 and/or the primary application system 208 from Step 1.

In both alternatives, the primary mobile smartphone application 206 will (with reference to FIG. 6) turn on the speakerphone(s) 608, microphone 606, turn up the volume 630, identify primary smartphone location (turning on location identification features if they are disabled 610, 612, 616), turn on camera 604 and snap pictures (not snapping pictures if video conferencing is selected) via the phone's API, group & link the information together and send it to the primary application server 208 via the notification system 670.

Step 4: Call Pickup and Information Viewing

There are three optional paths that stem from the two major alternatives from Step 3:

Alternative 1—Option 1: Primary smartphone application 206 automatically picks up phone call. For video conference viewing, primary smartphone application enables camera module 604 and automatically connects via video conference.

Alternative 1—Option 2: Secondary mobile application 204 and/or web portal interface 202 automatically picks up phone call. For video conference viewing, primary smartphone application 206 automatically connects via video conference. An indicator flag in the secondary mobile application 204 and/or web portal interface 202 informs the respective application to automatically pickup/connect.

Alternative 2: Secondary mobile application 204 and/or web portal interface 202 automatically picks up phone call. For video conference viewing, primary smartphone application 206 automatically connects via video conference. An indicator flag in the secondary mobile application 204 and/or web portal interface 202 informs the respective application to automatically pickup/connect.

In all three paths, the primary application system 208 will package up all the information gathered and sent from the primary smartphone 206 in Step 3 and make it available to authorized users 760 for viewing via the web portal interface 202 and/or the secondary mobile application 204. The information can be viewed simultaneously, before and/or after the call and/or video call is made.

In all three paths, the primary smartphone application 206 may also cause a loud ring and/or automated voice to inform user 750 that a direct connect is underway and also may cause the primary smartphone 206 to visually cue the user 750 through changes in color, text, vibration and/or possibly other cues.

FIG. 16 shows the process flow from initiation to connection, specifically illustrating how particular connectivity options for a direct connect described above may be selected by the collective system of the invention.

For example, the direct connection request has been received by the primary mobile application 206, perhaps through SMS or email electronic communication. The request may have come directly from the remote authorized user's 760 phone via the secondary mobile application 204 or through the primary application system 208 via the secondary mobile application 204 or from the web portal application interface 202. The monitoring process 650 of the primary mobile application 206 recognizes the direct connection request and triggers the intelligent event identification engine 710 to collect phone data around whether the primary phone 206 can connect to the Internet and if the connection is strong and fast enough.

If not able to connect or if connection is not sufficient, the monitoring process 650 would trigger the mobile application 206 to look up the phone number of the authorized remote caregiver 760 in the primary application data storage/database and initiate an audio/cellular call back to that phone number. In one instance, the requestor application (i.e., the secondary mobile application 204 and/or the web portal application 202), having flagged itself as attempting to direct connect to a particular phone in its own configuration, would identify the incoming phone number as belonging to the primary mobile application 206, recognizing it as pre-authorized, automatically answer the call. In another example, the phone could ring until the remote authorized user 760 picked up the auto-returned phone call.

In a separate example of a direct connection with an audio/cellular call back (as described above), instead of dialing the initiating remote authorized caregiver's phone 760, the primary mobile application 206 may dial a bridge number into the primary application system 208, which may then bridge dial the remote authorized user's phone through telephonic bridging/PBX (private branch exchange)/conferencing technology. Alternatively, the remote authorized user's phone 204 may already have dialed into the primary application system's 208 PBX/conferencing technology and be conferenced with the primary mobile phone 206.

In a different example, the primary application 206 may recognize Internet access as existent and sufficient, however the initiating secondary mobile application 204 may detect lack of Internet connectivity or sufficient Internet bandwidth/speed. In such an instance, the secondary mobile application 204 may initiate a cellular/audio-only direct connect to the primary mobile application 206 with a special flag indicating that an Internet connection will not suffice. The primary mobile application 206 will interpret the flag and not attempt an Internet, video and/or VOIP connection but only an audio/cellular direct connection as previously described.

In another example, Internet connectivity from both the initiating phone 204 or web application 202, as well as from the primary mobile application 206, is existent and sufficient. In this case, a call back is initiated by the primary mobile application 206 via its VOIP (voice over IP) client that connects to a VOIP server as part of the primary application system 208. The VOIP server also connects to the secondary mobile application 204 and/or the web application 202 in advance of notifying the primary mobile application 206, or after notifying, or after the primary mobile application 206 has a VOIP connection with the VOIP server. The VOIP server therefore bridges/creates the connection then between the primary mobile application 206 and the initiating secondary mobile application 204 and/or web application interface 202.

As described, a direct connect call results in creating a live phone call 514 and/or live video conference 504 without the user 750 of the primary mobile phone 206 taking action. As shown in FIG. 16, the type of call possible will depend on the quality of connection—if the cellular/internet connectivity is fast enough to support video calling that would take preference over or audio calling. In that case, as a backup, the system and method of the present invention uses a cellular audio call.

Internet existence and sufficiency is determined through API calls checking signal existence and strength of cellular Internet networks and wireless network detections. Pinging certain websites and/or servers using internet protocol calls and timing and comparing response rates is another method that may be used. Such checks are performed on both sides of the connection (the secondary mobile application 204 or web application 202 and the primary mobile application 206). Notifications are sent among systems using electronic communication—usually some/any combination of SMS texting, email and/or Internet protocol though also possibly via modem or other electronic communication methods that basic operating systems (and possibly their APIs) interact with. Audio calls and call answering are triggered through the device's APIs. VOIP/video conference connections may be established over Internet protocol through interfacing with VOIP clients and server APIs.

Figure 4:
FIG. 4 illustrates an exemplary direct connect call in accordance with the principles of the system and method of the present invention.

FIG. 4 provides an illustration of an instance of a direct connect call in place. In this example, a direct connect call has been initiated and is in session. The initiating user, through their web portal interface 202 and/or secondary mobile application 204 can see what the primary phone owner 406 is doing through the camera module 604 on the primary smartphone 206. The initiating user 760 is conversing 404 through the direct connection via the speakerphone 608 and microphone 606 on the primary smartphone 206 to the primary owner 406.

Figure 5:
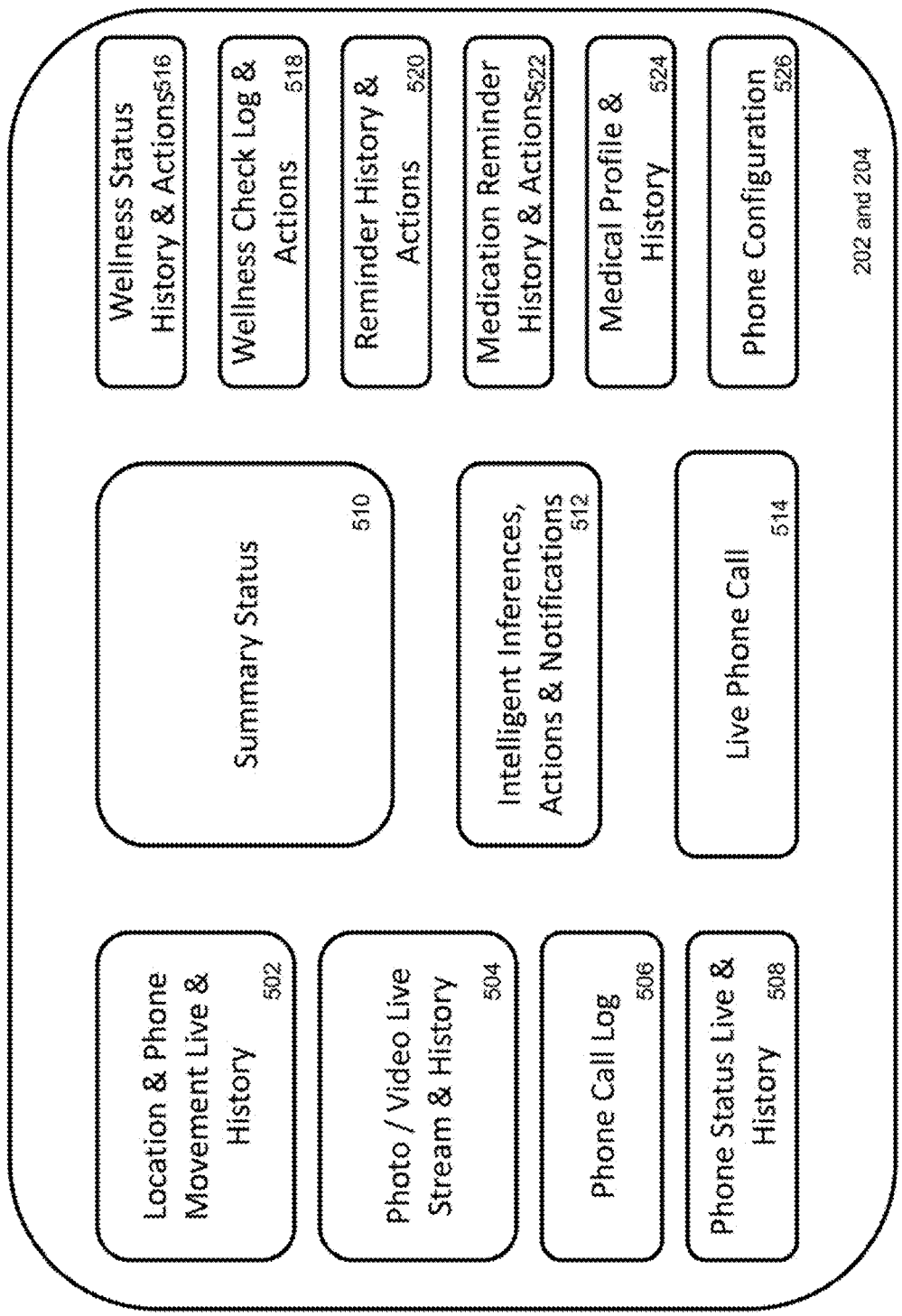
FIG. 5 depicts exemplary information provided to the web portal application and/or to the secondary mobile application in conjunction with a direct connect call in accordance with the principles of the system and method of the present invention.

FIG. 5 provides an illustration of exemplary information provided to the web portal application 202 and/or to the secondary mobile application 204 in conjunction with a direct connect call in one embodiment of the system and method of the present invention. This information is generally available to authorized remote users 760 who are logged into the web application interface 202 and/or secondary mobile application 204 at any time, including when the urgent notifications have been issued and otherwise.

The purpose of the information made available is to provide a broad and deep picture of what has been and is going on with the primary mobile phone application 206 and the primary mobile user 750 and to also help manage the daily caregiving features, urgent connectivity features, interface features and general phone features of the primary mobile application and primary mobile phone 206. The information can help determine the primary user's 750 whereabouts, their well being status (in part through status of status and/or wellness checks), indicate whether any (alarming) incidents occurred (such as dialing 911 and/or a fall detection) and related details; indicate whether they have been following certain patterns of behavior; and, indicating whether the phone 206 (and the user 750) have not moved for a period of time and/or that the phone 206 (and the user 750) did not reach an intended destination.

The information can also indicate whether the user 750 has indicated that they have been taking medication; whether the user 750 confirmed certain alarm reminders; whether the user 750 has been making phone calls—and to when and to whom they have been calling; whether or not the user 750 have been sending and/or receiving messages; and/or whether the phone battery died or the phone is not in signal range (cellular and/or internet cellular and/or Wi-Fi).

The information may also prompt the remote authorized user 760 to take action(s), which may include among the many actions described in the present invention: editing, altering, adding or removing reminders including medication reminders (such as taking, refilling and/or renewing medication), updating medical profile information, editing, altering, adding or removing particular automated wellness checks, setting location reminders, sending messages or information; updating or changing the primary mobile application 206 user interface, updating numbers for auto-conferencing on the primary mobile application 206, updating caregiver notification settings and so on.

This sample information, also illustrated in FIG. 5, is provided and accessible to the user 760 (e.g. caregiver or authorized user) who may be initiating a direct connect call on either the web portal application 202 and the secondary mobile application 204 and also to the primary smartphone user 750 on the web portal application 202 and the primary mobile application 206. The method and process of the invention calls for any and all of the information illustrated in FIG. 5 to be available. The sample information should not be construed as exhaustively conveying all possible relevant information being made available and those skilled in the art will recognize that other types of information may be shared without departing for the scope of the instant disclosure.

In further detail, the sample information may include in one embodiment of the system and method of the present invention (with reference to FIGS. 5 and 6):

a. The current and historical location and movement history 502 as determined through GPS 610, wireless 614, and/or cellular 616 location determination systems and accelerometer 612 logged with primary phone 206 date and time from internal clock 622 as periodically checked through the monitoring processes 650 and configured through the configuration processes 660 of the primary smartphone application 206. Additionally, location and movement history 502 may have photo and/or video snippets 504 tagged from the camera module 604 being engaged periodically by the monitoring processes 650 and configuration processes 660 that can be viewed. Location and movement history may be displayed in a textual format and/or via one or more markings or images of locations overlaid upon one or more map images. Furthermore, clicking on a particular location via a map or link or inputting a particular location into input fields on the primary web interface 202 and/or secondary mobile application 204 can search the historical logs/database 720 for other instances of the primary mobile application recording being at or around (within a predetermined distance radius) that location and return a listing of those instances with date/times, duration, and potential pictures and/or videos that may have been tagged and logged. The process flow for the logging process itself for most types of logging is shown and described in FIG. 21.

b. The phone call history log 506 of inbound, outbound, missed and connected calls may also be available for view. Those calls that were auto third party conferenced via the primary mobile application 206 may also be specially marked. Furthermore, clicking on a particular phone number or inputting a particular phone number into input field(s) on the primary web interface 202 and/or secondary mobile application 204 can search the historical logs/database 720 for other instances of the primary mobile application and or phone 206 recording making those phone calls and return a listing of those instances with date/times, duration, and potential location information that may have been tagged and logged. The logging process flow for most types of logging is shown and described in FIG. 21.

c. The current and historical phone status 508 of the primary smartphone application 206 may also be available. The basic logging process is shown and described in FIG. 21. The FEATURES logged may include current and historical information on the primary smartphone's 206 battery life, charging history, when the phone's signal status has been strong, weak or non-existent, availability of 3G and/or 4G networks, location date/time stamping as well as the current status of key phone features 602 which includes enabled or disabled status of camera module 604, microphone 606, speakerphones 608, GPS 610, accelerometer 612, wireless radio/LAN 614, cellular system 616, Bluetooth radio 618, touch screen 620, internal clock 622 and other relevant phone features 630.

The user 760 may be able to enable or disable any of these phone features remotely through the web portal application 204 and/or the secondary mobile application 204. Doing so consists of changes to the configuration files that get pushed to the primary smartphone 206 from the secondary mobile application 204 and/or the web portal application 202 and pushed through directly or via the primary application system 208.

d. A history of the outcome status of status and/or wellness check-ins 516 as well as a log of the status and wellness check-ins 518, including the questions, user responses and phone actions and corresponding notifications may also be available for view. Status and wellness checks are performed via the process shown and described in FIG. 19. As well, the information and status around any fall detection, phone shaking and/or 911 calls by the primary smartphone application 206 may be made available.

e. Urgent notifications. In the case of a fall/shaking, the primary smartphone fall detection process would be triggered. The process indicating how this is done is shown and described in FIG. 17. For example, if the phone 206 fell or was shaken, the phone 206 would recognize this event, and trigger a check to see if the user 750 has indeed fallen. The user 750 can indicate to the primary smartphone application 206 that they were alright, causing the alert to be dropped, but the event would still be logged in the system. In a different scenario, if the phone 206 fell or was shaken and the user 750 did not respond or did respond but responded negatively, that response information as well as the details around the phone calls and/or notification(s) initiated by the primary smartphone application 206 would also be made available.

f. A history of alerts and reminders 520 for the primary smartphone user 750 as well as medication reminders 522, the primary smartphone user's 750 responses and any notification(s) and/or subsequent action(s) that the primary smartphone application 206 may have taken based on user responses may also be available.

g. The primary smartphone application's 206 medical profile 524 and history of changes to the medical profile 524 as well as any medication reminder history 522 and changes may be made available.

h. The current configuration 526 of the primary smartphone application 206, which includes settings around the user interface, settings for urgent connectivity and monitoring as well as settings for non-urgent, daily interactions may also be available for viewing and altering. Any changes made on the web portal application 202 and/or secondary mobile application 204 are saved as configuration file changes and pushed out to the primary mobile application 206 to incorporate the new configuration changes either directly or through the primary application system 208.

A novel portion of the system and method of the present invention are the monitoring processes that look, listen for and act on a series of triggers, including but not limited to: primary phone/application usage 206, remote authorized user interactions 760, and location-based and other situational triggers, including potentially urgent situations. These triggers, in combination with the monitoring processes allow for the unique and high level of caregiving interactivity described. Below is further detail around the monitoring processes.

Figure 6:
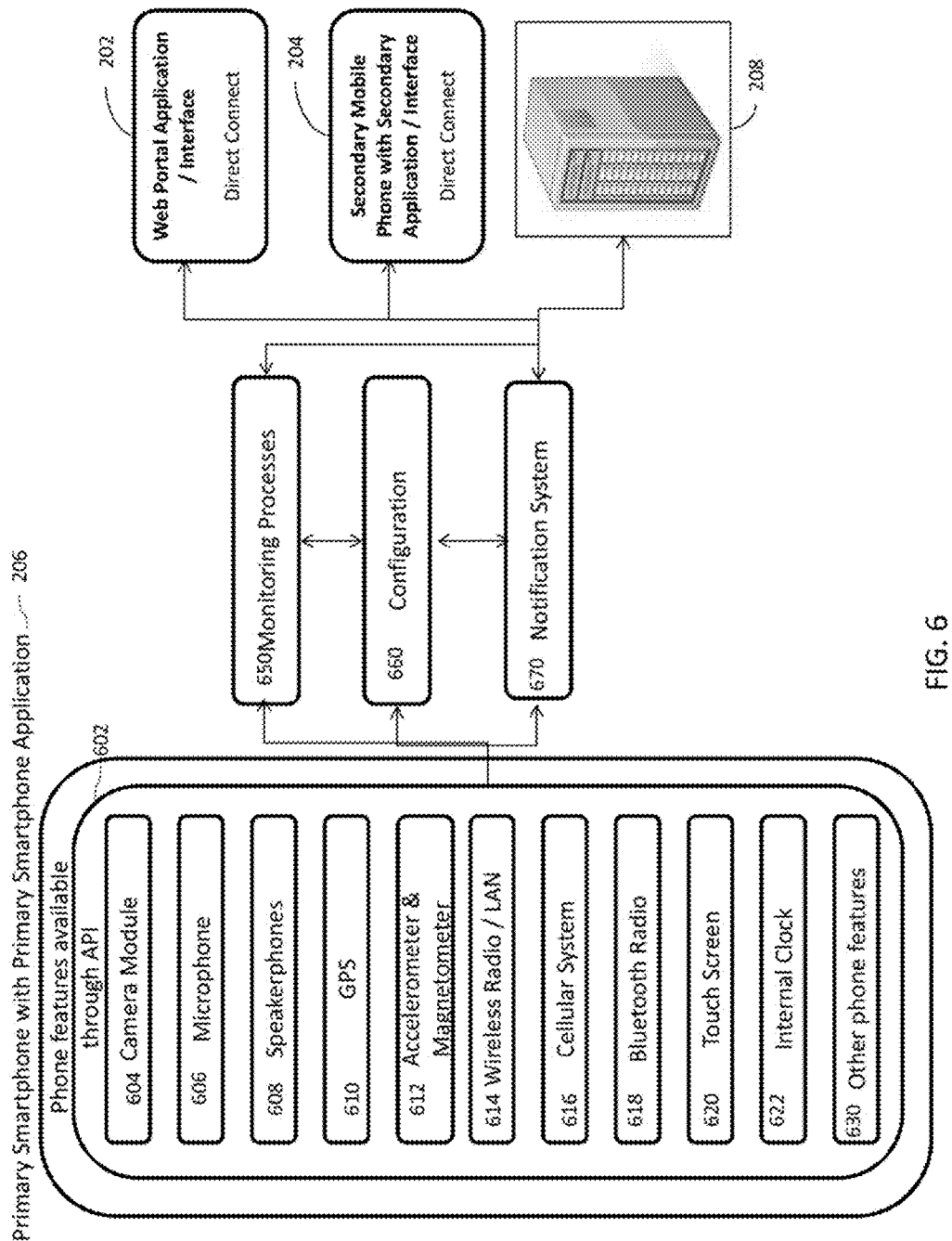
FIG. 6 is a flowchart showing the monitoring and notification processes in accordance with the principles of the system and method of the present invention.

FIG. 6 illustrates the monitoring and notification process components and steps. Illustrative flows for sample monitoring processes are shown in FIG. 17 and FIG. 18.

Figure 7:
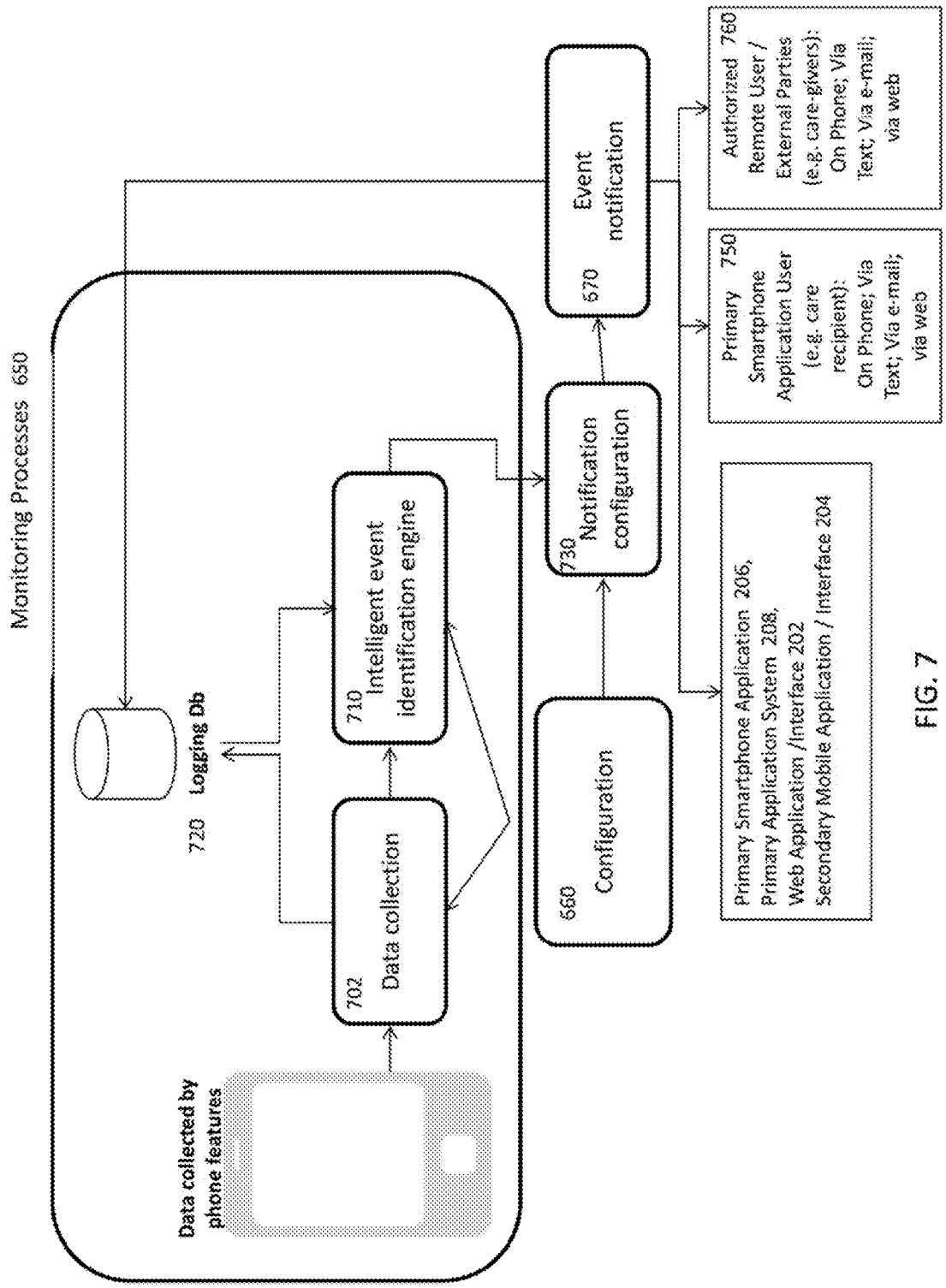
FIG. 7 is a flowchart showing further detail of the monitoring processes and event notification process of FIG. 6 in accordance with the principles of the system and method of the present invention.

FIG. 7 further illustrates the internal detail of the monitoring processes and event notification process.

Figure 8:
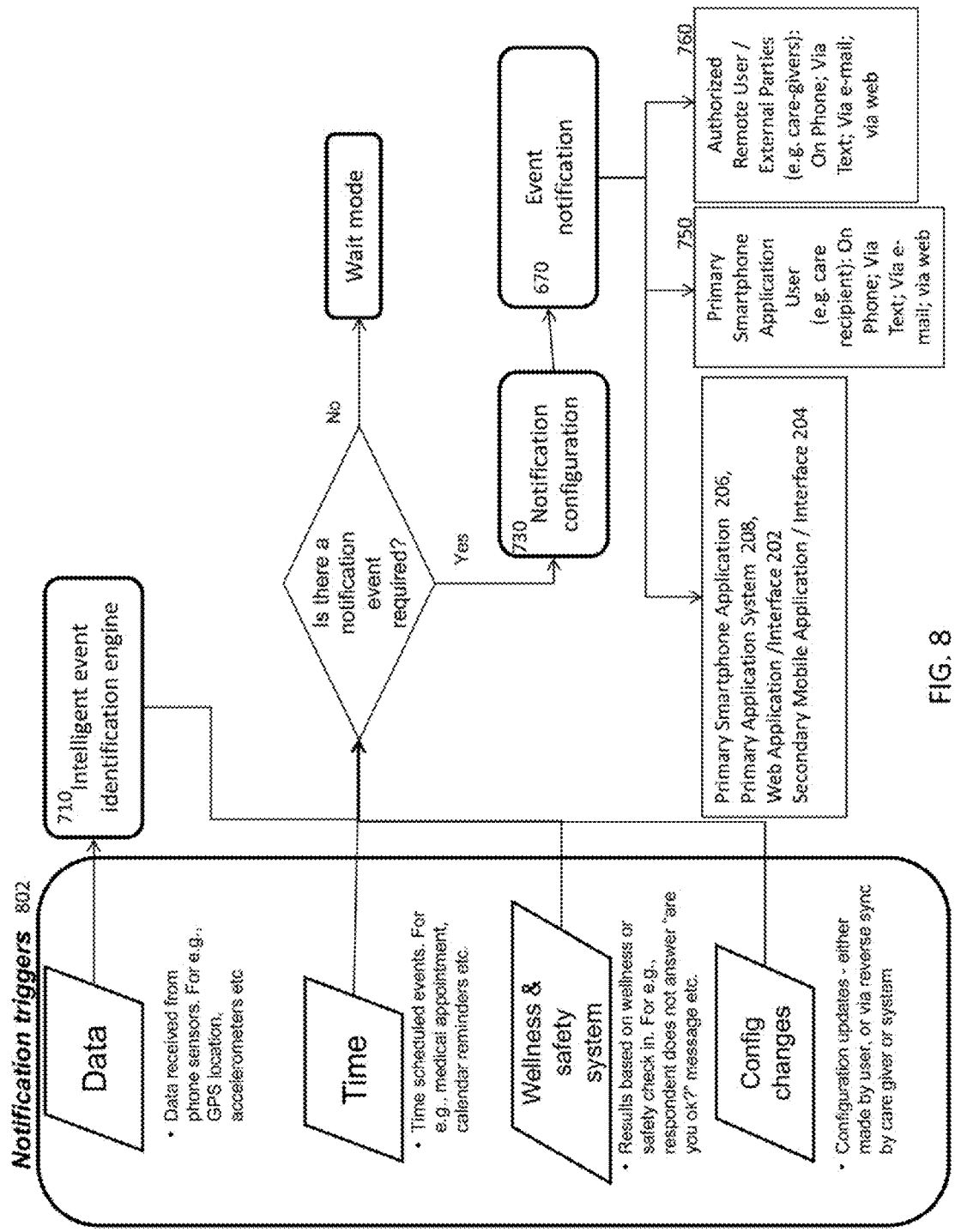
FIG. 8 is a flowchart showing exemplary notification triggers used by the monitoring processes in accordance with the principles of the system and method of the present invention.

FIG. 8 illustrates examples of notification triggers used by the monitoring processes. FIG. 20 shows the notification process.

The monitoring processes 650 digests the data collected 702 from the various described phone features 602 and other relevant phone features 630. This data collected 702 includes current and historical status of the various monitoring processes 650 as they are configured 660. An intelligent event identification engine (IEIE) 710 looks for pattern matches against predetermined scenarios and rules set in the configuration 660 and monitoring processes 650 engines. The IEIE 710 may be setup to utilize various rules and analysis to help in capturing events.

For example, the IEIE 710 can compare a series of readings collected from the location sensor to identify locations visited in the day. In another example, the IEIE 710 can evaluate data from accelerometers to identify movement (e.g., is the user moving?). That information is then processed for appropriate event notification 670 based on notification configuration 730. The intelligent inferences themselves 512 as well as the notification events 670 that occurred based on the inferences 512 may be made available.

The intelligent inferences themselves 512 may also be used as triggers to create notification or other events 670, including initiate a direct connection to authorized remote users 760 or other relevant parties, including 911 or urgent call centers, and/or to trigger some other monitoring process 650, logging event 720 and/or trigger some other action within the primary smartphone application 206, primary application system 208, the web portal application 202, and/or the secondary mobile application 204.

Included here are a series of disclosed embodiments of the invention that utilize the specialized monitoring processes 650 and the intelligent event identification engine 710. These embodiments are not exhaustive, but are a sampling of the kind of unique capabilities of the system and methods described here.

In the disclosed embodiment of the invention, the primary phone 206 hasn't moved for several hours during the day—this is called an "idleness" situation. The monitoring process 650 records movement at several intervals and compares each as shown and described in FIG. 18. The idle behavior is identified by comparing the location of the primary smartphone with previous location readings. Location readings are taken according to a polling frequency for collecting location data (here PFREQ) and stores those location readings in a log, via the process identified in FIG. 21. If the location has been the same or within a proximate distance defined as within LOCATION_RANGE and a time period equal or greater than that defined in TGT_PERIOD has elapsed, the system identifies this as an "idle situation." Otherwise, if distance is not within the LOCATION_RANGE, the phone is considered to have moved and the process is reset for the next PFREQ. If the distance is within the LOCATION_RANGE but the TGT_PERIOD has not been reached, the monitoring process will wait for further data points.

Once an "idle situation" is determined, the information is logged as an idle event in the primary mobile application system. The information is logged in the system log, potentially transmitted as an event notification to the primary application system 208 and an idle status check is initiated. The idle check is an interactive messaging to the user 750 and may involve validating with the user their status (asking if they are alright, indicating that the phone hasn't moved in TGT_PERIOD) and creating notifications for the appropriate recipients. If the user indicates they are ok and/or have moved in the TGT_PERIOD, the system goes back to waiting for the next reading according to PFREQ. If the user does not indicate that they are alright or indicates a negative response, then the system may perform other notification events to authorized users 760 and/or 911 based on the primary smartphone application's 206 configuration.

In this example, the monitoring process 650 recognizes that both location and phone position haven't moved. It also may recognize that there has not been user activity on the phone 260 in the form of moving or carrying the phone 260, making phone calls, or navigating in the phone in any way. Other data points may also be considered into the idleness assessment.

For example, the monitoring process 650 also may recognize that on that particular day or date during that particular time period, the phone 260 is normally at or near a different location (perhaps at a particular address). This is done by the IEIE 710 through a comparison of historical data—dates, times and locations and looking for patterns in movement to the same locations and deviations from those patterns. It may also recognize that an authorized remote user 760 (e.g. caregiver) has specified that if the phone 260 doesn't move during that period of time then to notify specified contacts registered in the configuration 660 and in the primary smartphone application 206. Examples of contacts—authorized remote users 760—include, but are not limited too, that remote user 760, other remote users, family, friends, professional caregivers, medical providers, medical centers, specialized living facilities and/or urgent call centers.

The intelligent event identification engine 710 recognizes these patterns and makes inferences that lead to notification of specified contacts and/or a wellness/status check-in, direct connection, and or other action of the primary smartphone application 206 to the primary smartphone application user 750. The responses of that user 750 are processed and may lead to a notification of specified contacts, logging to be made available for further monitoring processes 650 to leverage the intelligent event identification engine 710, direct connection and/or other actions specified in the primary smartphone application 206.

In the disclosed embodiment of the invention, the primary smartphone application 206 monitoring processes 650 recognizes that the phone 260 hasn't reached a destination that it regularly does during that date, day and/or time period or a location that was specified by an authorized remote user 760 in the configuration 660. The monitoring processes 650 may also record lack of movement and/or other indicators that a problem may exist. The intelligent event identification engine 710 will identify pattern matches of problems and/or look for specific problems and take appropriate actions and notifications as specified in the primary smartphone application 206, possibly including but not limited to wellness/status check-ins and/or creating a direct connection.

In the disclosed embodiment of the system and method of the present invention, the monitoring processes 650 record movement of the phone 260 over time. Based on the frequency and pattern of location and/or accelerometer (positioning) movement, the intelligent event identification engine 710 may infer that the user 750 is walking versus driving or vice versa. That information may then be recorded for further inferences by the intelligent event identification engine 710 or used to notify authorized parties, direct connect, automated check-in and/or take some other action of the primary smartphone application 206.

In the disclosed embodiment of the system and method of the present invention, the monitoring processes 650 record movement of the phone 260 over time. The monitoring processes 650 may also cause the phone's camera module 604 to record one or more photographs and/or video. The primary smartphone application 206 may recognize the photo as dark, and the intelligent event identification engine 710 may recognize that a dark picture along with the frequency and positioning of the primary smartphone as determined by the GPS 610, accelerometer 612, wireless radio/WAN 614 and cellular system 616 imply that the primary smartphone application user 750 is a walking and may be carrying the primary smartphone in a bag or purse.

In the disclosed embodiment of the system and method of the present invention, camera module 604 is used to take a picture of a prescription, perhaps on a prescription bottle or carton or any other medium. The monitoring processes 650 and specifically the intelligent event identification engine 710 can use image character recognition and determine that the contents of the image are, indeed a prescription based on characteristics common to all prescriptions (such as medication name, dosage, frequency, number of refills, prescribing physician, etc.). The primary smartphone application 206 will then automatically directly through notification to the primary application system 208 may electronically contact the pharmacy and/or medical practice to request a refill and/or renewal. The prescription information could also be redirected to create medication reminder alerts to take and/or to refill that particular medication using the alerts capabilities of the primary smartphone application 206 and/or to update the medical profile on the primary smartphone application 206 and/or other third party software.

In the disclosed embodiment of the system and method of the present invention, the monitoring processes 650 may monitor the primary smartphone's battery for dissipation status and patterns of dissipation that may correlate with various dates, days and/or times. Similarly, the monitoring processes 650 may monitor the primary smartphone's signal strength for patterns of signal strength and loss based on location pattern and/or date, day and/or time. In both situations, the intelligent event identification engine 710 may look for patterns to anticipate for the primary smartphone application 206 user when the battery might run low and/or signal strength might dissipate. In anticipating such an event, an event notification 670 may be triggered to notify the primary smartphone application user 750 and/or authorized external parties 760 and may direct specific action (such as ringing the primary smartphone application user and telling user visually and/or audibly to plug in the phone and/or to make any necessary calls now perhaps with reasons as to anticipated future phone status—depending on the situation).

The same monitoring process 650 and intelligent event identification engine 710 are also used in several of the features of the invention described in the instant application.

In the disclosed embodiment of the system and method of the present invention, cellular and Internet connectivity to a mobile phone can be established automatically and/or remotely when the mobile phone has been idle, not having had a cellular and/or Internet connection for some period.

In such instances a primary application system 208 will send an electronic notification to the primary mobile smartphone 206 via one or a combination of methods such as SMS text message, cellular call, VOIP call, email or Internet connection. The primary mobile smartphone application 206 will recognize the source of the call as being from the primary application system 208, as pre-configured in the software and will immediately initiate Internet protocol communication to the primary application system 208 and/or cellular communication to the phone's cellular network. If a connection cannot be made immediately, the primary smartphone application 206+ can be configured to periodically re-attempt both connection types (Internet and/or cellular connection) until contact is made.

In the disclosed embodiment of the system and method of the present invention, the system and method of the present invention is configured to periodically and/or through a series of predetermined times and/or via a pre-determined trigger(s) 802 (as identified in the monitoring processes 650) automatically turn on the mobile phone's location positioning features (e.g., such as GPS, multilateration of radio signals, and/or other mobile positioning technologies) if location positioning features had been off, then, once on, log the phone's location position with a date/time stamp, optionally automatically snap picture(s) and/or video(s) and send all that linked data/information via Internet, cellular or other remote electronic connection to another user via an Internet website, an email, text message and/or other form of electronic message.

In the disclosed embodiment of the system and method of the present invention, the system and method of the present invention is configured to automatically send an event notification 670 (in the form of a call, electronic and/or otherwise or subsequent notification, action and/or trigger) to the primary smartphone application 206, the primary smartphone application user 750, the primary application system 208, the secondary smartphone application 204, the web portal interface 202 and/or to an authorized external party 760 (e.g., 911, an urgent call center and/or authorized care providers and/or an Internet site) if the mobile phone 260 is dropped, has not been moved or moved from a geographical location for a predetermined amount of time, if the phone has not reached a predetermined geographical destination by a certain date and time, if the mobile user 750 has not "checked in" by pressing a special button on the phone 260, by not satisfactorily answering a wellness check or mobile medical survey on the mobile phone 260 and/or by pressing a button on a separate wireless device linked/connected with the mobile phone 260. All of these notification triggers 802 are recognized through the intelligent event identification engine 710 and processed accordingly. The monitoring process 650 will recognize if any kind of action or notification event required, partly based on the notification configuration 730. If so, an event notification 670 may be triggered.

Figure 9:
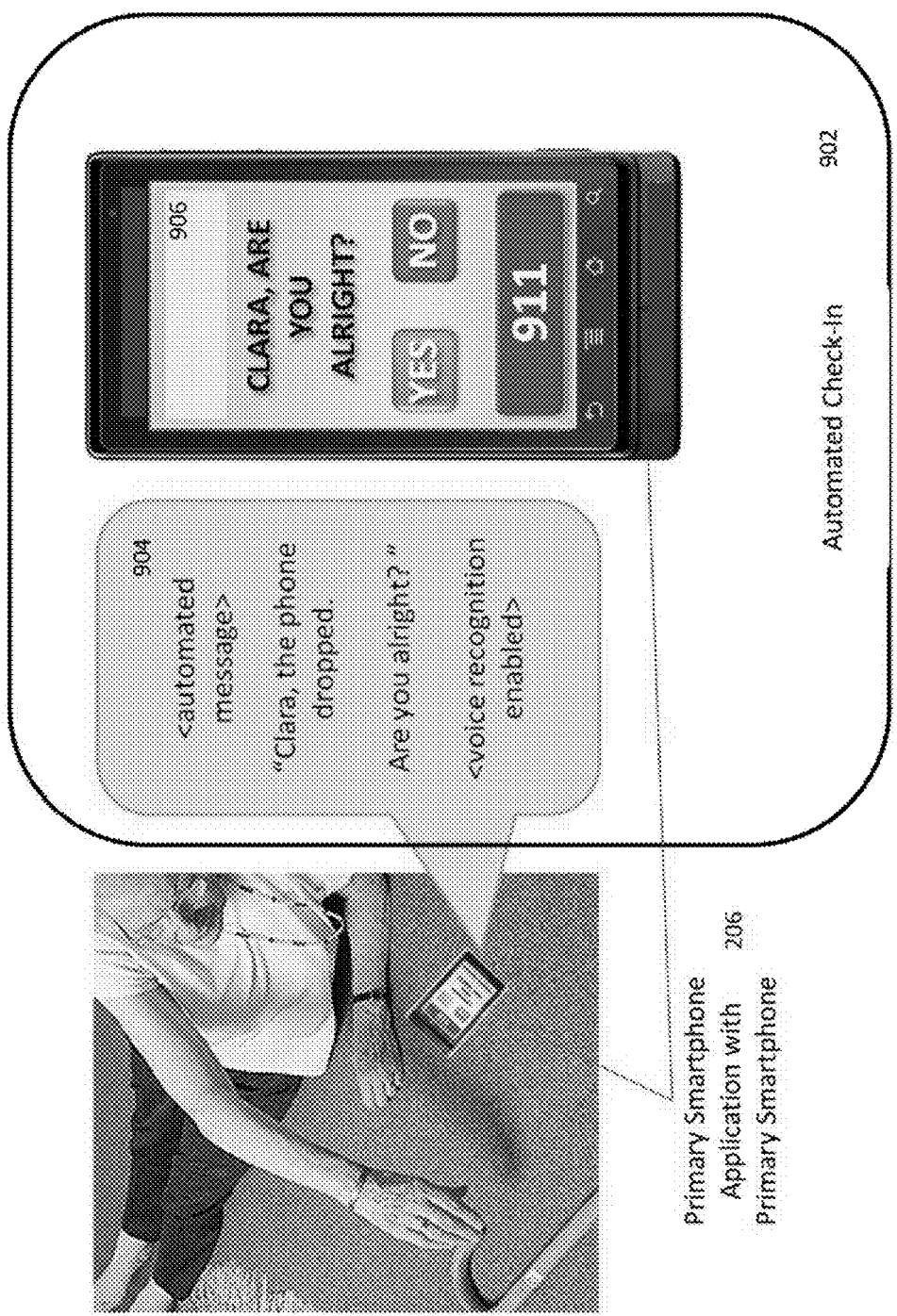
FIG. 9 depicts an example of a fall detected by the primary smartphone application that then triggers an automatic check-in in accordance with the principles of the system and method of the present invention.

The primary smartphone mobile application 206 can be configured to remain in a listening status via its monitoring processes 650 to automatically take action (as defined above) upon one or more of the following occurring:

- A drop in altitude that meets "falling" criteria. The primary smartphone mobile application 206 can be configured to sense a drop in altitude using the smartphone's accelerometer/gyroscopic technologies 612. Falling criteria can be defined to include the rate of drop, the estimated distance dropped and positioning change parameters of the primary smartphone as determined by the phone's accelerometer 612. The detailed process for identifying a fall is shown and described in FIG. 17. As shown in FIG. 9, a fall is detected by the smartphone application 206 and it initiates an automatic check-in 902 which has both a visual/interactive component 906 and an audio/voice recognition component 904. The monitoring process 650 listens for both physical responses to the touchscreen in 906, audio responses via voice recognition 904 as well as complete lack of response. In any or all of these cases, a negative and/or lack of response may result in an automatic dial to an urgent response center or 911 as well as an automatic notification to authorized user(s).
- Idleness. The primary smartphone application 206 can also be configured using the smartphone's location positioning technologies 610, 614, 616 and/or the accelerometer/gyroscopic capabilities 612 to sense whether the phone 260 has been moved. The smartphone application 206 can also be set with criteria for determining whether an alert should be made based on the amount of time the phone has been idle and/or the location of the phone's idleness.
- Location alerts. The smartphone application 206 can be configured to alert for notification if the smartphone 206 is moved from a particular geographic location/locations and/or too a particular geographic location/locations.
- Lack of check-in/button press. The primary smartphone application system 206 can require a user 750 to press a pre-determined button within a pre-set time parameter. If the user 750 does not press/click the button (physical and/or virtual button), the application alerts for notification events 670. The process followed in this case mirrors the process for idleness check as shown and described in FIG. 18.
- Specific responses to wellness checks/surveys. The smartphone application system 206 can provide a survey of questions to the user 750. Based on preset criteria, specific responses (in the form of button presses and/or clicks and/or input information) or lack of response to the system can cause an alert for notification. The wellness check is a time-based user configurable event executed as shown in FIG. 19.

The mobile application system 206 can be configured to immediately notify user(s) 750, 760 and/or primary application system 208 immediately upon one of the foregoing events occurring and/or initiate an inquiry to the mobile user 750 and/or remote user 760 to check on the primary mobile application user's 750 status. For example, the mobile application can ask the user 750 if they are alright visually and/or audibly through texts, pictures, voice and/or rings/alarms and then listen for a response via a button press and/or audio response (possibly using voice recognition) input of the monitoring processes 650. If the inquiry response is negative or there is no response, the application system can then notify the authorized user(s) 750 and/or 760 and/or primary application systems 206 and/or 208 for further action. Notification can be in any combination of the forms described above as well as logged 720 for future access by authorized user(s) 750, 760. The notification process flow for the primary smartphone/application is shown and described in FIG. 20.

Notifications can be automated, periodic events or asynchronous events caused by the primary smartphone application 206 monitoring processes or through interactions or physical requests from primary mobile application users 750 and/or remote authorized users 760 as described in this document and in the description of log triggering events in FIG. 21. As illustrated in FIG. 20, a notification event is triggered. The monitoring processes will first identify recipients that are flagged to be notified for that particular notification event based on the primary smartphone application's configuration. The monitoring process will then determine if the notification is flagged as a critical event notification. If it is, the notification will be sent to the predetermined recipients 750,760 either directly and/or through the primary application server 208. It will then return to the home or previous state.

If the notification event is not flagged as a critical notification, then the monitoring process will check if the SYNC_PERIOD time interval has been reached. If not, the monitoring process will wait until the SYNC_PERIOD time interval has been reached. Once the SYNC_PERIOD time interval has been has been reached, the monitoring process will check the battery status. If the battery power is below a minimum threshold, BATT_MIN, the notification event will be logged and queued for the monitoring process to attempt at the next SYNC_PERIOD time interval. If the battery power is sufficient (at or greater than BATT_MIN), then the monitoring process will confirm whether any kind of call (regular or direct connect) is in session with the primary smartphone. If the primary smartphone application 206 is unable to send the notification event while a call is in session, it will log the event and queue it to send either when the call is completed or at the next SYNC_PERIOD.

If the primary smartphone application 206 can send during a call or if the primary smartphone 206 is not in a call, then the notification will be sent to the identified recipients 750,760 either directly and/or through the primary application server 208 and the phone will then return to the home or previous state.

FIG. 21 is a flowchart illustrating the logging process in accordance with the principles of the system and method of the present invention. The flowchart illustrates the process for how the system and method of the present invention determines the timing and actions of a logging event. As illustrated, there are three main triggers that cause a logging event:

Option A. A predetermined time schedule determines periodic logging. LOGPERIOD denotes the time between logging runs as stored in the primary smartphone application 206 database. The monitoring processes described in FIG. 7 recognize when a scheduled logging is going to occur. For example, LOGPERIOD could be set at every hour, at which time, the data called for to be logged in that log type is pooled together.

Option B. A change or event-driven log. Examples include but are not limited to logging the responses of a wellness check, logging if a user shakes the primary mobile smartphone 206 to indicate an urgent 911 dial or dials 911 directly or through hot button, logging a fall detection and user responses, and/or logging reminders and user responses.

Option C. An authorized remote user 750, such as a caregiver, can request a log of certain data related to the primary smartphone application 206—including, but not limited to: phone movement history (such as GPS/location movement), phone logging, data around delivery and responses to wellness checks and/or reminders (including medication-related reminders), phone idleness, any alerts, etc. An example of when this might be attempted if a caregiver was concerned about the primary smartphone application user 750 and the data visible, as illustrated in FIG. 5, was not as recent as the caregiver would like. In this case, the caregiver could press a button on their secondary mobile application 204 or the Internet portal application 202 and trigger a collection of data to be logged and sent to the primary application system 208 to be viewed on either system (202, 204).

Each notification trigger of any notification trigger type will have FEATURES of data and information to be collected and logged. The monitoring processes include preconfigured definitions of these triggers and the data to be collected in regard to each. For example, a periodic log may track location movement (e.g. GPS or other location-determining system), phone movement (even if in same location), capture photos and/or video to link with the location and phone movement and a date/time stamp. The monitoring processes recognize the different data requirements of that log (as determined in the configuration.

The monitoring processes will then look at the status of the battery life of the primary smartphone to see if the battery life is greater than a minimum power requirement, BATT_MIN. If the battery is below the BATT_MIN level, the primary smartphone application 206 will add a local log on the primary smartphone application database indicating battery is too low to send the pooled data to the primary application server 208. It will abort the log attempt. However, in a slightly altered version, if the primary smartphone application determines that the primary smartphone has enough battery to send a basic message around the battery log but not enough battery to send the larger pooled data collection, it may send a notification message to the primary application server 208 indicating as such.

If there is enough battery power, the monitoring processes will then determine whether the primary smartphone is on a call—cellular or Internet/VOIP—based, including whether it is a standard, typical phone call or a direct-connect call as described in this application. If any call type is in session, the primary smartphone application 206 will wait for a period of time to re-attempt the call logging action, as defined in LOG_REATTEMPT. This assumes that the primary smartphone application 206 is unable to log data at the same time a call is in session. If the smartphone allows the data to be logged while a call is in session and/or if the mobile carrier allows for data to be separately sent while in a call, then this step can be bypassed.

The monitoring processes of the primary smartphone application 206 will then collect the data regarding the identified FEATURES. The monitoring processes will turn on (if necessary) any primary smartphone hardware or software component such as those identified in 602 or primary smartphone application feature necessary to collect that data and then collect the data. Otherwise, the data will simply be collected from the data store in the primary mobile application 206.

The data will then be written to the system log of the primary mobile application 206. It may also be sent to the primary application server 208 as a notification event. The primary application will then return to the previous state of the application prior to the logging event.

The monitoring process for identifying a fall is illustrated in FIG. 17. In this example, the primary smartphone application 206 is actively listening and collecting the phone's accelerometer/orientation/positioning information according to a predefined interval, PFREQ, and storing the data in a log for comparison on the primary smartphone application 206. The application 206 is then comparing the log of the data (accelerometer/orientation/positioning data) and determining whether the difference in the movement data points over a predetermined period of time PREQ is equal to or greater than ACCEL_MAX, indicating a high acceleration to warrant a consideration of a falling event.

Similarly, the application 206 is then comparing the log of the data (accelerometer/orientation/positioning data) and determining whether the vertical height location difference is equal to or greater than HGHT_MAX, indicating that the fall was from a large enough height to consider it a falling event for the purposes of checking-in with the phone user 750.

If neither ACCEL_MAX or HGHT_MAX criteria are met, the monitoring processes continue to listen for further events. However, if both criteria as described are met, then a falling event is stored in the log on the primary mobile application 206 and potentially sent to the Primary Application System (PAS) 208. The user 750 is then prompted to see if they are alright. If the user responds they are alright, then the monitoring process resets and waits for the next event. If the user indicates they are not alright or does not respond at all, the monitoring process logs event locally and may create a notification event to inform the PAS 208, authorized remote user(s) 760 and/or 911.

In the disclosed embodiment of the system and method of the present invention, the system and method of the present invention is configured to automatically notify specified users 760 (e.g., care providers) via web portal application 202 and secondary mobile application 204 if calls are made to a predetermined list of phone number(s). For example, automatically notify authorized users 760 (via call, electronic message or otherwise) when the mobile user's doctors, nurses, therapists, etc. are dialed and called—and then log 720 and/or send that information with date/time stamp via Internet and/or cellular network using email, SMS, Internet upload or other electronic connectivity.

The smartphone application software 206 can be configured to take specialized action based on a user making calls to certain phone numbers and/or specified users. The actions can include notification events 670 (e.g. call, electronic message or otherwise) to authorized user(s) 750, 760, as well as logging of information in the primary system for later access by authorized user(s). To initiate a third party conference or to take other kinds of actions described here, the monitoring processes 650 check call attempts against the configuration setup 660 and matching numbers result in an event notification 670 to corresponding systems and parties 202, 204, 206, 208, 760 based on notification configuration 730.

In the disclosed embodiment of the system and method of the present invention, the system and method of the present invention is configured to automatically party conference the mobile phone 206 with pre-determined specified user(s)/care provider(s) 760 via telephonic and or Internet connectivity (cellular, VOIP, hybrid cellular-VOIP, PBX and/or other call conferencing technology) when calls are made to specific, predetermined phone number(s). The smartphone application system 206 can be pre-configured and/or updated through the configuration process 660 with specific phone numbers that when dialed from the primary smartphone 206 result in a party-line conference call to pre-determined specified user(s) 760 via telephonic and/or Internet connectivity.

Figure 10:
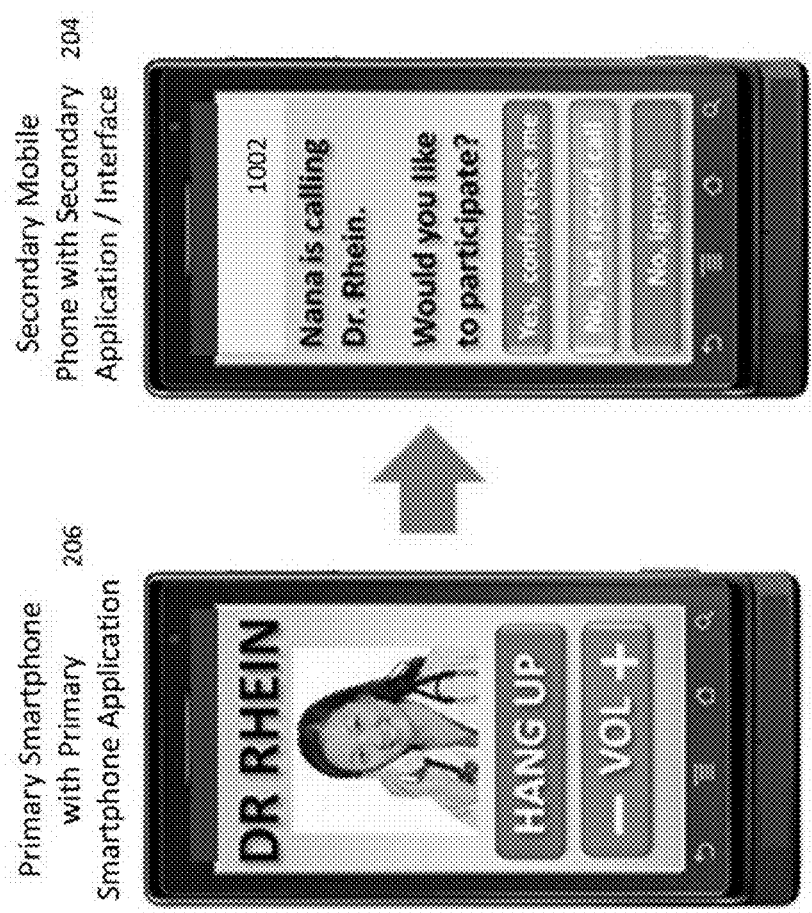
FIG. 10 depicts exemplary interfaces of the primary smartphone application and the secondary smartphone application for purposes of establishing a conference call with authorized third party based on a call by the primary smartphone application to a predetermined phone number in accordance with the principles of the system and method of the present invention.

FIG. 10 illustrates an example of the interactivity between the primary smartphone application 206 and the secondary smartphone application 204 of the invention for purposes of establishing a conference call with authorized third party 760 based on a call by the primary smartphone application 206 to a predetermined phone number.

In one example, a call to predetermined phone number results in a notification to an authorized third party 760 via SMS, email or secondary mobile application 204. The secondary mobile application will receive a notification with optional response button(s) 1002. Clicking the response buttons 1002 results in either direct notification to the primary smartphone application 206 via electronic communication (SMS, internet, or other) causing the primary smartphone 206 to auto conference the secondary mobile application's 204 phone number or indirect notification to the primary smartphone application 206 via electronic communication (SMS, internet or other) to the primary application system 208 that notifies the primary smartphone application 206 to initiate a conference call inclusive of the secondary smartphone/application 204 and the intended phone number. Alternatively, the primary application system 208 may initiate the party conference to the primary smartphone/application 206, the secondary smartphone/application 204 and the intended phone number.

It should be noted that all embodiments of the method and system descried in the instant application related to auto conferencing should be construed to include conferencing in pre-authorized users 760 on any phone in addition or substitution to a secondary mobile application 204 phone and/or to the pre-authorized user's 760 web portal application 202. However, the secondary mobile application 204 and the web portal application 202 allows for the interactivity of response 1002, including but not limited to prompting the pre-authorized user to be conference called by the system 206, 208 or possibly to have the primary smartphone application 206 or primary application system 208 record the phone call or simply ignore the call. This type of interactive response may also be achieved by other phones not running the secondary smartphone application software 204 through either specific text/SMS interaction and responses and /or audio request with voice recognition and/or number responses on the phone keypad that are interpreted by the primary smartphone application 206 and/or primary application system 208 to take one or any of the actions described above.

The conferencing process of the system may work as described above and/or in one or a combination of the following three methods:

Option 1: The primary smartphone application system 206 uses the cellular network's party conference capability to automatically dial the number being called as well as the pre-authorized user(s) 760.

Option 2: The primary smartphone application 206 does not actually dial the number specified but alternatively dials a different phone number that connects with a remote application system 208 (via cellular, Internet and/or hybrid cellular-Internet method or other). The remote application system 208 creates a party conference with the primary smartphone 206 user 750, the originally intended phone number and the pre-authorized user(s) 760.

In either process, the primary smartphone application 206 will send an electronic notification to the remote application system 208 either before making the call (as in Option 1) or upon pressing the dial button (as in Option 2). The remote application system 208 via monitoring processes 650 will then recognize the call as a party conference call, log the action request 720, optionally notify pre-authorized users 760 via electronic application notification, text and/or email and/or other notification event 670 and initiate the telephone calls.

Option 3: Upon pressing the dial button, the initiating primary smartphone application 206 first sends a notification to pre-configured authorized user(s) 760 phones (which as previously described may or may not use a secondary mobile application 204 or web portal application 202) as well as to a remote application system 208 via electronic data and/or telephonic means (including using cellular, Internet, and/or hybrid cellular-Internet means). The authorized user(s) 760 may see the action being initiated through a secondary remote application 204 on their mobile phone and/or via a text message, email, Internet web portal 202 and/or other electronic and/or telephonic notification. The authorized user(s) 760 can then respond to the notification to:

A. Allow or not allow the original intended call to be placed, and/or

B. Participate or not participate via party conference in the original call to be placed and/or C. Have the primary smartphone application 206 or the primary application system 208 record the call for future reference.

If the authorized user 760 responds that they would not like the call to be placed, the call is not placed and the original user 750 may be notified via the primary smartphone application 206, the remote application system 208 and/or directly via an electronic and/or telephonic means to the initiating primary smartphone 206.

If the authorized user 760 responds that they would like to participate in the call, the electronic and/or telephone response is sent either directly to the initiating primary smartphone 206 or indirectly via the remote application system 208. At that point, the party conference can be created either directly from the initiating primary smartphone 206 (as described in Option 1) or from the remote application system 208 (as described in Option 2).

Using either process, the smartphone application 206 can be set to automatically record the conversation via the primary smartphone application 206 or the primary application system 208. Either system can also be set to automatically send notification 670 using the same means as described herein.

Figure 11:
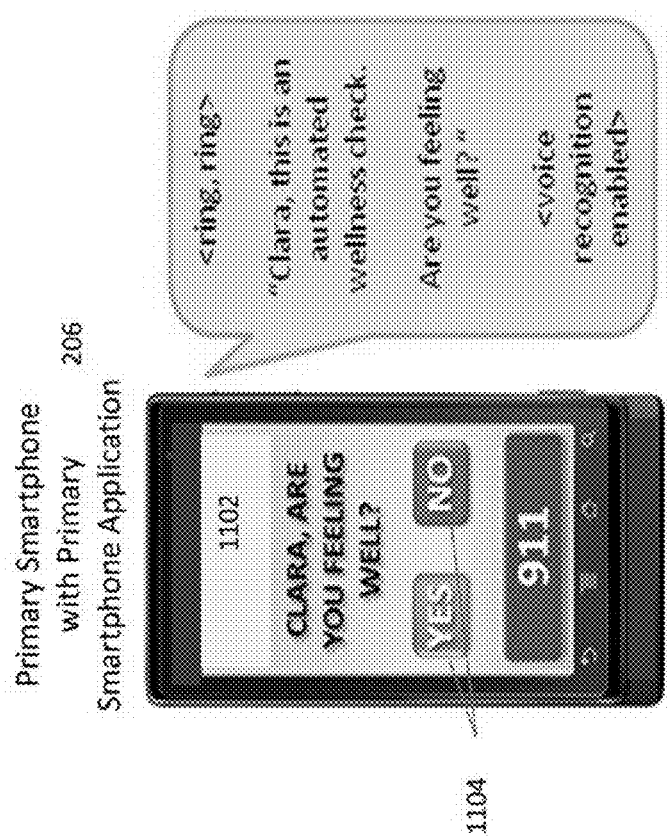
FIG. 11 depicts an exemplary automated wellness check question in accordance with the principles of the system and method of the present invention.

In the disclosed embodiment of the system and method of the present invention, the system and method of the present invention is configured to allow the primary mobile user 750 or an authorized user/care provider 760 to create custom, automated wellness checks or surveys that the mobile user 750 responds to once or periodically and which can have custom actions associated with particular responses and/or results based on software customization. FIG. 11 illustrates an example of an automated wellness check question according to the principles of the system and method of the present invention.

Examples of particular automated notification events 670 by the software would be electronic notification to authorized caregivers and/or notification to urgent response center and/or 911 760 containing or providing access to survey results, medical or other information, including software-triggered recommendations, mobile phone location tracking information, pictures, audio and/or video captured from the mobile phone 206.

The system and method of the present invention is configured such that a user 750, 760 can create a series of questions/surveys 1102 for the primary mobile smartphone application 206 that have pre-configured response actions 1104. The response inputs 1104 can vary in number and type—such as a button selection, menu list selection and/or text input. The user 750 can input information via touch and/or voice response recognition. The primary smartphone application 206 will record and log the responses along with a date/time stamp and electronically send the information for data collection 702 to a remote application system 208 to be monitored 550 by the intelligent event identification engine 710 and for access via a web portal 202 and/or secondary remote mobile application 204 by authorized user(s) 750, 760.

Certain specific responses 1104 and/or response patterns recognized by the intelligent event identification engine 710 can be set 730 to initiate selective actions/event notifications 670, such as urgent notification to 911 and/or an urgent response center and/or authorized user(s) 760. Other actions include special instructions provided to the primary smartphone user 750, location tracking initiated and information sent to pre-authorized user(s) 760, camera enabled and pictures to be automatically taken via camera module 604 and sent or live video conference initiated to pre-authorized user(s) 760 and/or direct connect capabilities initiated (as described herein).

It will be appreciated by those skilled in the art that the survey(s) can be created on the primary smartphone 206 itself and/or on a remote application system 202, 204 by an authorized user(s) 760 that then gets uploaded electronically to the primary smartphone application 206. The survey(s) can be configured 660 to be asked at a particular date/time and/or periodically via preset days, times and/or periods of time that authorized user(s) 750, 760 configure. The survey(s) can be saved on the remote application system 208 where they can be enabled and/or disabled, saved for later use, and/or reconfigured or re-customized.

FIG. 19 is a flowchart illustrating the process followed to execute, collect and log answers for a safety or wellness check in accordance with the principles of the system and method of the present invention. According to a predefined time periods SFREQ and/or WFREQ, a particular safety and/or wellness check is initiated according to the monitoring processes. The primary smartphone application user 750 will responds to the series of questions as described, with each question and answer being logged accordingly in the primary application system 206. As described individual and/or collective answers options can be preconfigured to trigger a notification event, including to authorized remote users 760. If the user responds to a question or series of questions that trigger notification (possibly a "negative response" indicating they do not feel alright) then an event notification is created and triggered to notify the primary application system 208, authorized remote users 750 and/or possibly 911. However if the response(s) do not trigger a notification event, then the responses are logged and the system either continues to ask further questions of the safety/wellness check or completes the status/wellness check and logs the response locally on the primary smartphone application 206 and may send information to primary application system 208.

Figure 12:
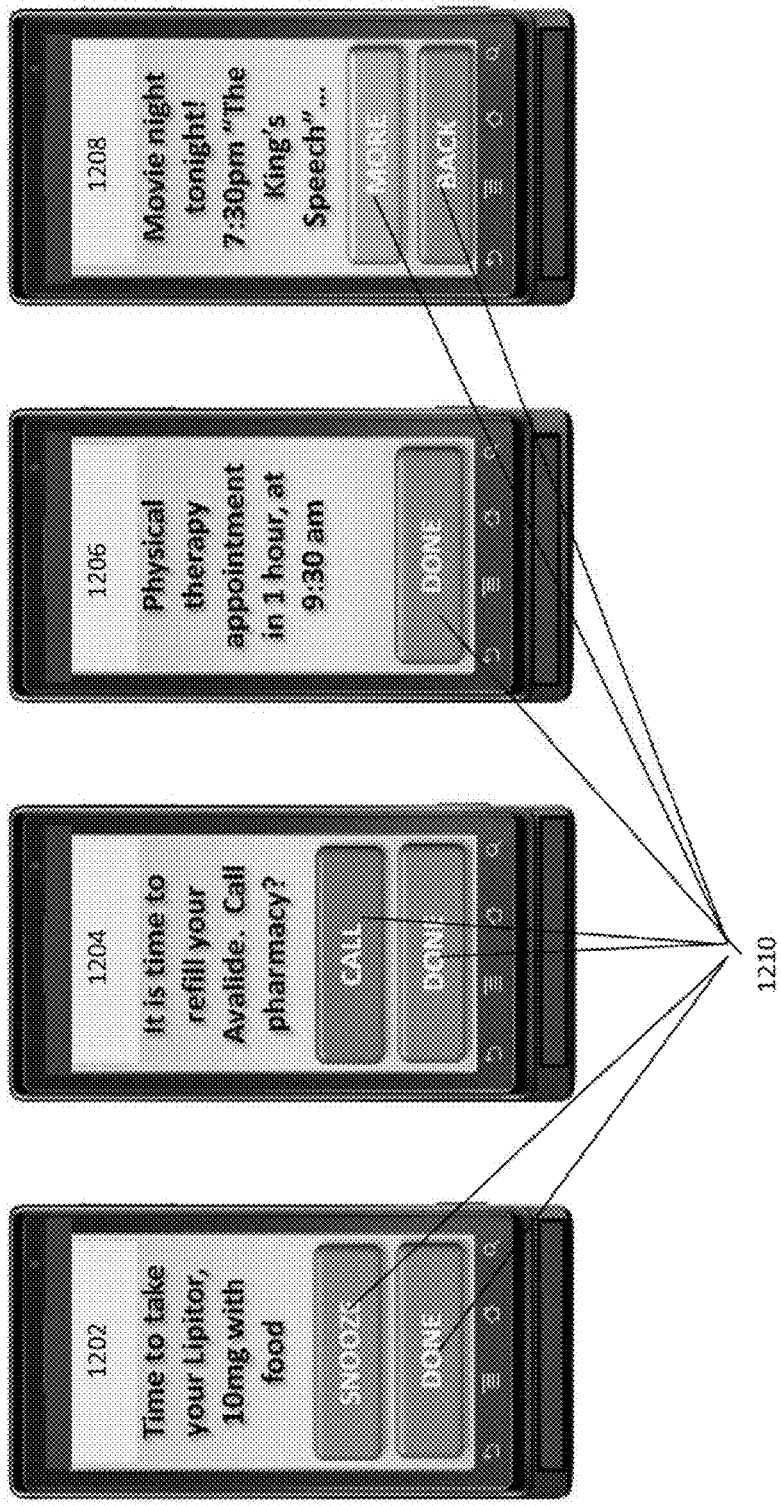
FIG. 12 depicts a series of exemplary interfaces on the primary smartphone application for a plurality of the caregiving features in accordance with the principles of the system and method of the present invention.

In the disclosed embodiment of the system and method of the present invention, the system and method of the present invention is configured to provide caregiving features to a primary smartphone application user 750 through a primary mobile smartphone 206 and/or remote Internet application 202, 208 and/or secondary mobile application 204, including but not limited to those mentioned elsewhere in the application as well as those mentioned below. FIG. 12 illustrates exemplary interfaces on the primary smartphone application 206 for some of the caregiving features described according to the principles of the system and method of the present invention. FIG. 12 specifically illustrates examples of medically-related instructions, specialized alarms, medication tracking & renewal/refill reminders and potential actions/hot buttons that can be defined and used according to the principles of the system and method of the present invention.

a. Medically-related instructions including therapy and medication instructions or other information, news and/or instructions 1208 relevant to the primary smartphone user 750 sent to mobile user 750 by authorized remote user/caregiver or authorized medical provider 760. Examples of other kinds of information 1208 include addresses, driving directions and/or other instructions.

b. Specialized alarms, alerts and schedules 1202, 1204, 1206 that notify the primary smartphone user 750 of appointments and provide related, relevant information. For example, an appointment reminder 1206 that also includes instructions on diet and driving directions linked together and then logged on the primary mobile phone application 206 and primary application system 208 and via Internet with date/time stamp, the type of alert or alarm, the information linked with alarm and the mobile user's response (such as acknowledgement of the alarm). These alarms, alerts & schedules are specialized notification objects that may contain the standard event information (such as date/time, subject, description, alarm repeat information & duration) as well as having an active status (active or inactive), specialized system messages and trigger links Some of the trigger links may be tied to the user interface, such as with action buttons beyond the usual confirmation, snooze and cancel buttons. These notification objects are incorporated into the monitoring processes 650 and intelligent event identification engine 710 and could be linked with actions/notification events 670 that can be taken. Examples include a medication refill alert that prompts the user 750 to push a button to directly call the user's preferred pharmacy, the phone number of which is stored and specially flagged in the database by the primary mobile application 206. In another similar example, a medication renewal alert may prompt a button that directly calls the prescribing physician, whose information is stored and linked with the medication in the medical profile data of the primary mobile application 206. It could be that the phone number for that physician is also, separately, flagged for auto third party conferencing of a specified remote authorized user 760. Upon pressing the call button, the primary mobile application 206 will call the physician and go through the auto third party notification and conferencing process described previously in this application. In another example, a medication, refill or renewal reminder will have an option for the user 750 to select that they no longer take that medication. Doing so may stop any further alarm reminders that the system was configured to deliver by removing the alert, causing it to be inactive or removing any future repeat configurations on the alert. It may also cause notification to remote authorized caregivers 760 as previously described. These alarms, alerts and schedules can be setup on the primary mobile phone 206 itself or remotely through a cellular and/or Internet connection by the user 750 and/or by an authorized user/caregiver 750.

c. Medication tracking features that notify primary application user 750 when time to take a medication, and/or when a medication refill and/or medication renewal is approaching 1204 and whether a refill is available. These medication tracking features are incorporated into the monitoring processes 650 and intelligent event identification engine 710 and can be linked with actions/notification events 670 that can be taken. For example, the primary mobile application 206 and/or the primary application system 208 can automatically request a refill and/or renewal on medications or can prompt the mobile user 750 to have the system 206, 208 automatically request a refill and/or renewal to the physician(s) and/or preferred pharmacy via pressing an action button 1210 or through voice recognition on the primary smartphone application 206 according to profile as stored in the primary user's configuration 660. The system and method of the present invention is configured to log the events, information and associated actions via the data collection process 702 for reference by the primary user 750 and/or by an authorized user/caregiver 760. These medication tracking features and actions can be setup directly on the primary mobile phone application 206 or remotely through a cellular and/or Internet connection by an authorized user/caregiver 750 using the web portal 202 and/or the secondary smartphone application 204.

d. Specialized hot buttons dialers for initiating calls to urgent calls to 911 and/or urgent response centers, different operators, concierge service and/or other service providers. Once pressed, these buttons not only connect user 750 to 911 and/or urgent response centers (or other intended receiver), it also causes notification 670 to authorized users/caregiver(s) 760 and a logging of event 720 for view by primary smartphone user 750 and/or authorized remote users 760. These button(s) can be graphical action buttons on the primary mobile phone screen similar to those in 1210 or buttons located outside the screen on the primary mobile phone 206 itself.

e. A series of pre-customized texts that the primary mobile user 750 can use to communicate with authorized users/caregivers and/or medical providers 760 without having to type an entire or portion of a text notification. These pre-customized texts can be customized on the primary mobile phone application 206 or remotely on the web portal interface 202 and/or secondary mobile phone 204 by an authorized user/caregiver 760 and electronically sent through the configuration process 660 back to the primary mobile phone application 206 for use with text, email and/or other messaging features utilized by the primary mobile phone application 206.

f. Specialized web/Internet 202 and mobile phone portals 204 for administrative and caregiving access and interaction with the primary mobile smartphone application 206 and among authorized remote users 760 by a primary mobile user's 750 medical providers, living facility administration, urgent response centers, other lifestyle and/or application providers and authorized caregivers 760. Different kinds of authorized remote users 760 may have their own specialized interface to those applications 202, 204.

As mentioned above, FIG. 5 illustrates exemplary features that a specialized caregiving Internet portal 202 and secondary caregiver mobile phone application 204 has in the disclosed embodiment of the system and method of the present invention. Such a portal 202 and/or mobile phone application 204 preferably are accessible through both secure Internet and mobile applications, allowing authorized users/caregivers 760 to interact with the primary smartphone user 750 via the primary smartphone application 206. Preferably, authorized users/caregivers 760 are allowed to update the primary smartphone application settings remotely—such as the phone book 526, medical profile 524, calendar appointments 520, 522, location tracking interval settings 502, 504, call recording and notification settings 504, 512, 516, 518, 520, 522, 526, urgent notification settings 502,512, 516, 518, 520, 522, 524, 526 and usability settings 526 such as changing colors, font size, ring and volume options or others described in the other claims of this application. It could also be used to send information to the primary smartphone application 206— such as instructions for taking medication or driving directions.

Examples of remote authorized users 760 might include, but are not limited to: family, volunteer caregivers, occupational therapists, medical providers, and/or independent living facility staff.

The remote application system 208, caregiver portal 202 and/or the secondary mobile applications 204 allow the primary mobile user 750 and remote authorized users 760 to also get in touch with the larger caregiver community. Authorized users/caregivers 760 can interact with one another, sharing advice or tips. Such users can also find technical assistance.

In one embodiment of the system and method of the present invention, the secondary mobile application 204, with some and/or all of its described functionality, can co-exist on the primary mobile phone 206 and be used in conjunction with the primary mobile phone application 206. Similarly, a primary mobile phone user 750 can also serve the role of an authorized remote user 760 and vice versa in various situations. For example, a spouse can act as both a care receiver 750 and a caregiver 760. Those skilled in the art will appreciate that all embodiments, methods, systems and/or processes described in the instant application should be construed also incorporating the possibility of this dual role.

In the disclosed embodiment of the system and method of the present invention, the system and method of the present invention is configured such that web portal 202 and the secondary smartphone application 204 provides access to a storefront for obtaining the system software solutions and related cellular hardware, services and accessories.

One embodiment of the system and method of the present invention further comprises a radio alert connectivity device 1302 that, when activated, sends a signal to its host radio-enabled mobile phone 206 (e.g., via Bluetooth 618 or other radio 616, 630) to dial a predetermined number and/or connect via secure Internet connection to a predetermined application and/or call center and/or other authorized user 760.

Figure 13:
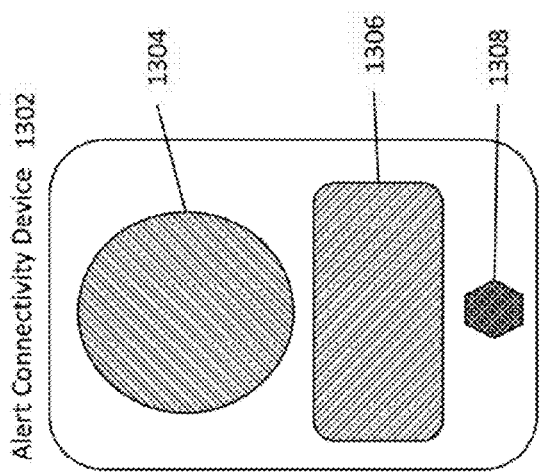
FIG. 13 depicts a front view of an exemplary radio alert connectivity device in accordance with the principles of the system and method of the present invention.

FIG. 13 illustrates an example of a radio alert connectivity device according to the principles of the system and method of the present invention. In addition to containing a radio 1308 for communicating with the primary smartphone application 206, the alert connectivity device 1302 also contains a microphone 1306 and speakerphone 1304 that can be used to listen and speak with primary phone user 750 as well as the remotely authorized person/call center 760 to whom the primary smartphone application and phone 206 are connected. The device 1302 also initiates location tracking of the primary smartphone device 206, message notifications 670 (via text, email or Internet) to authorized third parties 760 and picture and/or video capture & send notifications 670. Essentially, the device 1320 turns the primary smartphone 206 into a mobile Personal Emergency Response System (PERS).

As discussed above, the system and method of the present invention comprises software among the primary system application 208, the web application 202 and the secondary mobile application 204 configured to remotely customize the primary mobile phone application 206—including font size, screen colors, volume, creating and setting custom alarms with calling actions, creating and setting custom surveys with calling actions, editing/updating phone contact information, medical profile, turning on/off certain features as well as interacting with the primary smartphone 206 via the methods described in all the claims in this application. Configuration changes and setup are made via the interfaces of the web portal application 202 and/or the secondary mobile application 204. The information is captured and pushed either directly to the primary mobile application 206 or indirectly to the primary application system 208 which may either push the changes through to the primary mobile application 206 real time and/or wait for a synchronization event between the primary mobile application 206 and the primary application system 208 to occur. The primary application system 208 will treat the setup and configuration changes as data collected 702 and log the information in the logging database 720 for the monitoring processes 650, for viewing by primary users 750 and authorized remote users 760 and to eventually push to and synchronize with the primary smartphone application 206 any changes made directly on the primary smartphone application 206 itself.

Figure 14:
FIG. 14 depicts a series of exemplary interfaces on the primary smartphone application for medical profile in accordance with the principles of the system and method of the present invention.

In the disclosed embodiment of the system and method of the present invention, the system and method of the present invention is configured to maintain a medical profile of the primary mobile user 750 on the primary mobile phone application 206 that can be accessed and/or updated on the mobile phone 206 itself or remotely via cellular and/or Internet connection by authorized users for use by the primary mobile application 206. FIG. 14 illustrates an exemplary interface showing how a medical profile might function on the primary smartphone application 206. In one embodiment, a sticker on the back of the phone 206 provides easy instructions for quick access to the medical profile.

A medical profile can include, but is not limited to, information such as medical conditions, allergies and/or drug sensitivities, reactions, medical devices, medications, blood type and/or other relevant patient information for reference in urgent and non-urgent medical situations. The profile can be updated by authorized users 750, 760 on the primary smartphone application 206 or remotely through the secure remote application system 208 including an Internet web portal 202 and/or secondary mobile application 204. Certain parts of the medical profile can be flagged in the application's database by the user to be shown on the home screen and/or locked screen of the primary mobile application 206.

In the disclosed embodiment of the system and method of the present invention, the system and method of the present invention is configured to recognize a shaking pattern and/or a voice (through voice recognition) that results in the primary mobile phone 206 answering the phone and/or resulting in taking other pre-determined actions 670 (instead of pushing a button to answer the phone or take an action).

A predefined physical shaking pattern is into the primary mobile smartphone application 206, which then senses changes in movement based on the accelerometer/gyroscopic technology 612 embedded in the phone. In a process similar to the fall detection monitoring process shown and described in FIG. 17, if the primary mobile user 750 shakes the phone 206 in a manner consistent with a predefined pattern in which acceleration timing is greater than a minimum, pre-defined value and direction change indicates a pattern of movement over a short distance (less than a pre-defined value), followed abruptly by inverted movement over a similar short distance, and then repeated at minimum a number of predefined number of times, the primary mobile smartphone application 206 can recognize the pattern via the monitoring processes 650 and the intelligent event identification engine 710 and take predetermined actions 670, such as answering an incoming call and/or taking the response to mean an answer to a question such as "yes" or "no" to a phone survey (as described elsewhere in the instant application) or to initiate a call to a phone number (such as 911 or an urgent call center) that has been pre-linked to a particular pattern.

In the disclosed embodiment of the invention, the primary mobile smartphone application 206 can prompt the mobile user 750 for whether they would like to answer the phone, dial a user and/or take similar action and then utilize established voice recognition (VR) technology via APIs into that VR software to await a predetermined voice response (such as "Yes" or "Answer"). Using the monitoring processes 650 previously described, the intelligent event identification engine 710 can recognize and match the pattern it sees, consult the configuration 660 and create appropriate event notifications 670.

In the disclosed embodiment of the invention, the primary mobile smartphone application 206 and/or the secondary mobile application 204 is configured to allow the mobile user (750,760) to switch back-and-forth between standard telephonic, cellular-based audio phone connectivity and a VOIP/Internet-based audio and/or video connection, including while a phone call is underway or while it may appear to the user that the phone call is underway.

FIG. 1 shows an example of this functionality and FIG. 22a illustrates the process of the system and method of the present invention for switching from a standard telephonic, cellular-based audio phone call to an Internet-based, VOIP connection that allows both audio and/or video connectivity while a standard, telephonic, cellular-based audio phone call is underway within the application system.

FIG. 22b illustrates the process of the system and method of the present invention for switching from an Internet-based/VOIP connection to a standard telephonic, cellular-based audio phone call while an Internet-based/VOIP connection is underway within the application system.

While a call is underway, the user 750, 760 can switch among a standard telephonic, cellular-based audio call, a VOIP-based audio call and a VOIP-based audio/video call. This is initiated by either the primary mobile user 750 pressing a button to switch (as illustrated in FIG. 1) on the primary mobile application 206 in-call screen or by a remote user, such as a remote authorized user 760, pressing a similar button on their in-call screen of the secondary mobile application 204, the web portal application interface 202, and/or a special version of a secondary mobile application 204 that is designed specifically for (possibly non-authorized) remote users in order to leverage the video streaming/VOIP client that the primary application system 208 utilizes and requires to make a video/VOIP call. Such as connection switch between audio and/or video and audio may be accomplished as follows:

When the existing call is standard telephonic, cellular-based audio call and the "initiating" user clicks to switch to either a VOIP-based audio or audio/video call, the process of the system and method of the present invention, as illustrated in FIG. 22*a* is as follows:

When the initiating user is in a standard telephonic, cellular-based audio call, they will have the option to select a button that indicates they can switch to a VOIP call (and possibly given choice whether to maintain audio only or go to video and audio VOIP call). The VOIP call button is only active if the local application (which could be 204 or 206) of the initiating user has that particular contact in the phonebook flagged in the local database as having VOIP access. Alternatively, the local application can check that the remote application has VOIP connectivity after the initiating user clicks on the switch button. Upon clicking, the switch button, the application may confirm intentions with the initiating user. A positive response results in the initiating application 204,206 showing a message to initiating user to wait while the VOIP connection is established. The initiating application's 204 or 206 VOIP client will then initiate a VOIP connection to the same contact as the telephonic phone number as linked in the local application 204 or 206 database. This will be accomplished through the primary application server's (PAS) 208 VOIP server. The PAS 208 will electronically confirm the "recipient" mobile application's status of its VOIP client to confirm that it exists, is enabled and possibly that it is connected to the Internet and possibly the strength of connection.

If unable to confirm these facets, the PAS 208 will send an electronic message to the initiating mobile application 204, 206 that the other party does not have VOIP available and the standard, telephonic audio call will continue. If the call has already been dropped for any reason (including dropped by the initiating application 204, 206 in order to attempt a VOIP connection), then the message from the PAS will trigger the initiating application 204, 206 to auto-dial the original contact phone number and the recipient mobile application 204, 206 will recognize the phone number and may automatically pick-up the standard, telephonic phone call.

If the PAS 208 is able to confirm that the recipient mobile application's 204, 206 VOIP client's status (i.e., that it exists, is enabled and possibly that it is connected to the Internet and possibly connection strength) then the PAS's 208 VOIP server will reach out to the recipient application's 204, 206 VOIP client and establish a bridge connection with the initiating application's 204, 206 VOIP client.

At any point after initiating the switch, either the initiating mobile application 204, 206 or the PAS 208 will have notified the recipient remote application 204,206 to disconnect the standard telephonic audio call and enable, if disabled, the recipient mobile application's 204, 206 VOIP client. If the notification came from the initiating mobile application 204, 206, then the initiating mobile application 204, 206 will also disconnect the audio call on its own phone. If the notification came from the PAS 208, the PAS 208 will also notify the initiating mobile application 204, 206 to disconnect from the standard telephonic call, likely after confirming that a VOIP connection could be established.

When the existing call is a VOIP-based audio or audio/video call and the initiating user wants to switch between VOIP-based audio and audio/video, the VOIP connection will toggle back and forth in what is an established process for the VOIP connection.

When the existing call is a VOIP-based audio or audio/video call and the initiating user wants to switch to a standard telephonic, cellular-based audio call (perhaps because the Internet connection is not strong at the moment and the initiating mobile application 204, 206 indicates to user that cellular signal strength is strong), the initiating user clicks on a button to switch during the call and the process of the system and method of the present invention, as illustrated in FIG. 22*b*, is as follows:

When the initiating user is in a VOIP-based audio or audio/video call, they will have the option to select a button that indicates they can switch to a standard telephonic, audio-based cellular call. Upon clicking, the switch button, the application may confirm intentions with the initiating user. A positive response will cause the initiating application 204,206 to then check whether a cellular signal is available (and possibly strong enough). If not, a message will indicate this to the user and the existing VOIP-based call will continue. Alternatively, initiating application 204,206 could continuously check status of cellular signal and disable switch when cellular signal is not available.

Assuming the cellular signal is present (and possibly strong enough), the initiating application 204,206 will message the initiating user to wait while a standard call is established. The initiating application will then initiate a cellular call to the recipient application's 204,206 phone.

If both initiating and recipient application's 204,206 are able to maintain both a VOIP connection and standard cellular connection simultaneously, then the recipient application 204,206 will recognize the phone number via the contact link in the application's 204,206 database and automatically pick up the phone. At that point, the VOIP connection could be dropped by the initiating application, the receiving application 204,206 or the PAS's 208 VOIP server.

If either the initiating or recipient application's 204,206 phone (or both) are unable to simultaneously maintain a VOIP connection and standard cellular connection simultaneously, then either the initiating application 204,206, the recipient application 204, 206 or the PAS 208 will cause the VOIP client to drop the connection prior to initiating the cellular call. The initiating mobile application 204, 206 would have electronically communicated the intention of the connection switch to both the PAS 208 and recipient application 204, 206 via electronic communication methods, possibly including via VOIP connection, other internet connection or SMS.

In the disclosed embodiment of the invention, VOIP calls can be made from the outset (not only switched during calls) via the primary mobile application 206, the secondary mobile application 204 and/or the web application system 202. The local phonebook database within all those applications is configured to register whether a contact has registered a compatible VOIP client with the PAS 208.

In the disclosed embodiment, the system and method of the present invention comprises the aggregated feature set and/or subsets of the capabilities and features described in this application, for use in connecting primary users 750 and authorized remote parties 760 (e.g. caregivers) with one another for urgent and non-urgent situations. The feature set includes but is not limited to audio and/or video direct connect, automated remote connectivity, automated call conferencing based on predetermined phone numbers, location tracking, automated picture and/or video sending/remote camera monitoring, automated location tracking with photo and/or video logging, intelligent monitoring of urgent and non-urgent situations, including but not limited to lack of movement with the primary mobile phone 206, lack of reaching a location by the primary mobile phone 206, automated fall detection, automated wellness checks/custom actionable surveys, as well as remotely updating and customizing the primary mobile phone application 206 from a secure Internet application 202 and/or secondary mobile applications 204 and a specialized user interface that compels the primary application user 750 to utilize their smartphone 206 though it is not required to make use of the application features described herein.

In the disclosed embodiment, the system and method of the present invention further comprises a unique purchase and installation process. In the disclosed embodiment, those wishing to purchase the software and/or devices compatible with the system and method of the instant invention can either call or visit a predetermined website 202. In the disclosed embodiment, there are two different paths depending on whether the user 750,760 does or does not already have an existing compatible device.

For users 750,760 who do not yet own a compatible device, there are five key steps to the purchase process:

1. Smartphone and cellular plan selection.
   The website makes recommendations for specific smartphones that have been thoroughly tested to be compatible with the system and method of the present invention. A secondary mobile application 204 can also be separately purchased and/or downloaded. The secondary mobile application 204 is not necessary for receiving text messages or calls on their cell phones.
2. User information gathering
   Information gathered includes:
   a. Primary User 750 contact information
   b. Authorized user(s)/Caregiver(s) 760 contact information (primary administrator and/or others)
   c. Preferences for customization 660 of primary smartphone application 206 information, including but not limited to: medical profile (if desired), any initial phonebook entries (doctors, caregivers, living facility, etc.), any automated reminders, automated wellness checks and wellness check content, caregiver notification options, phone tracking options for urgent situations (location tracking on/off, tracking intervals, call logging, camera picture snapping on/off, video conference options, simplified interface on/off, etc.) . . .
   Emails may be sent to the authorized remote user(s) 760 if provided in the setup process as well as possibly a unique code or series of codes via SMS or by calling the authorized remote user(s) 760 phone that will be required to be entered and match in order to help confirm their identification from two separate sources.
3. Consent and authorization forms
   Electronic disclaimers and authorization forms for primary users 750 and authorized user(s)/caregiver(s) 760. If the primary user 750 is not the purchaser or present on the phone when purchasing, they will need to authorize usage on their phone 206 when it is received.
4. Shipping & payment for any purchases, including but not limited to: primary smartphone and primary smartphone application 206 and/or secondary mobile smartphone and application 204.
   For new primary mobile phone 206 purchases, the primary mobile application 206 will be configured and customized so that the phone 206 is ready to go when the user 750 receives it. After a user 750, 760 has completed the order, they are presented with an optional online tutorial.
5. Phone arrival
   Once the primary smartphone with primary smartphone application 206 has arrived and the user 750, 760 turns it on, the primary smartphone application 206 will automatically run and initiate a "startup" process to activate the phone, provide electronic disclaimer/authorization, and to provide an optional tutorial to demonstrate how the phone works. Alternatively, the user 750, 760 may connect to a system operator for a talk-through demonstration and to answer any questions. The primary smartphone application 206 will have pre-installed all of the preference settings provided during the purchase process, which then can be adjusted at any time on the phone 206 or remotely by an authorized user/caregiver and/or company authorized operator 760.

If the primary user 750 already has a smartphone that is compatible with the primary smartphone application 206, they can go to an authorized marketplace to purchase and download the primary smartphone application software 206 to their smartphones. They then can visit a specific website 202 to provide additional user information, setup authorized user(s)/caregiver(s) 760, customize other user settings and purchase any additional hardware or accessories (as described above). Alternatively, the user can open the newly downloaded primary smartphone application 206 and/or secondary mobile phone application 204 which will also walk them through the setup process on the phone itself as well as provide the appropriate electronic disclaimer(s).

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

We claim:

1. A system for remote care and monitoring, comprising:
   a first mobile device for use by a first user;
   a second device for use by a second user; and
   a server, the server configured to communicate with the first mobile device and the second device;
   wherein the first mobile device is configured to detect and log information about the activity and inactivity of the first user, the activity and inactivity of the first user being determined by at least one of: at least one location of the first mobile device, at least one movement of the first mobile device, at least one picture automatically captured by the first mobile device, at least one video automatically captured by the first mobile device, at least one intended destination of the first mobile device, at least one response by the first user to at least one wellness check-in, at least one phone call of the first mobile device, at least one response by the first user to at least one medication reminder, at least one response by the first user to at least one alert, at least one fall detection of the first device, at least one idleness check of the first device, or at least one violation of a medical profile of the first user;

wherein the second device is configured to communicate with the first mobile device through the server to allow the second user to customize a user interface for the first user on the first mobile device;

wherein the second device is further configured to communicate with and monitor the first user through the first mobile device;

wherein the second device is further configured to control a plurality of functions of the first mobile device; and wherein the first mobile device is configured to automatically establish a live telephonic and/or voice-over-IP (VOIP) call comprising audio and/or video communications between the first user and the second user, the call being initiated by the second user through the second device and/or the server, and the call being automatically established without interaction by the first user with the first mobile device after the first mobile device authenticates the second user and validates that the second user has initiated the call.

2. The system for remote care and monitoring of claim 1 wherein the first mobile device is a smartphone.

3. The system for remote care and monitoring of claim 1 wherein the second device is a smartphone.

4. The system for remote care and monitoring of claim 1 wherein the second device is a computer.

5. The system for remote care and monitoring of claim 1 wherein the first mobile device is configured to communicate to the second user the information about the activity and inactivity of the first user.

6. The system for remote care and monitoring of claim 1 wherein the server is further configured to communicate to a third party the information about the activity and inactivity of the first user.

7. The system for remote care and monitoring of claim 1 wherein the first mobile device further comprises a monitoring process engine, the monitoring process engine configured to monitor the first user and the first mobile device.

8. The system for remote care and monitoring of claim 7 wherein the monitoring process engine is further configured to detect the activity and inactivity of the first user based on movement or non-movement of the first mobile device.

9. The system for remote care and monitoring of claim 1 wherein the first mobile device is further configured to automatically initiate a communication with the second user for the purpose of establishing a conference call between the first user, the second user and a third party when the first user initiates a call to the third party.

10. The system for remote care and monitoring of claim 1 wherein the first mobile device and the second device are configured to switch between cellular-based audio-only communications between the first user and the second user and Internet-based audio or audio-visual communications between the first user and the second user, the switch occurring during an existing call between the first user and the second user.

11. The system for remote care and monitoring of claim 7 wherein the monitoring process engine is further configured to monitor a schedule of the first user.

12. The system for remote care and monitoring of claim 7 wherein the monitoring process engine is further configured to monitor an operational status of the first mobile device.

13. The system for remote care and monitoring of claim 7 wherein the first mobile device further comprises an intelligent event identification engine in communication with the monitoring process engine, the intelligent event identification engine configured to automatically generate notifications based on information received from the monitoring process engine.

14. The system for remote care and monitoring of claim 13 wherein the notifications generated by the intelligent event identification engine are automatically communicated to the first user.

15. The system for remote care and monitoring of claim 13 wherein the notifications generated by the intelligent event identification engine are automatically communicated to the second user.

16. The system for remote care and monitoring of claim 13 wherein the notifications generated by the intelligent event identification engine are automatically communicated to a third party.

17. The system for remote care and monitoring of claim 7 wherein the first mobile device further comprises an intelligent event identification engine in communication with the monitoring process engine, the intelligent event identification engine configured to automatically activate features of the first mobile device based on information received from the monitoring process engine.

18. The system for remote care and monitoring of claim 17 wherein the features of the first mobile device automatically activated by the intelligent event identification engine comprise at least one of: a camera, a microphone, a speakerphone, a global positioning system, an accelerometer, a magnetometer, a wireless radio, a cellular system, a Bluetooth radio, a touch screen, an internal clock, a messaging system, or a calendar system.

19. The system for remote care and monitoring of claim 1 wherein the first mobile device is configured to automatically open a direct audio or audio-visual communication link with the second device when the first user does not respond to a communication request sent to the first mobile device.

20. A method for remote care and monitoring, the method comprising the steps of:
providing a primary mobile application for use on a first mobile device by a first user;
providing a secondary mobile application for use on a second device by a second user; and
providing a server, the server configured to communicate with the first mobile device and the second device;
wherein the first mobile device is configured to detect and log information about the activity and inactivity of the first user, the activity and inactivity of the first user being determined by at least one of: at least one location of the first mobile device, at least one movement of the first mobile device, at least one picture automatically captured by the first mobile device, at least one video automatically captured by the first mobile device, at least one intended destination of the first mobile device, at least one response by the first user to at least one wellness check-in, at least one phone call of the first mobile device, at least one response by the first user to at least one medication reminder, at least one response by the first user to at least one alert, at least one fall detection of the first device, at least one idleness check of the first device, or at least one violation of a medical profile of the first user;

wherein the second device is configured to communicate with the first mobile device through the server to allow the second user to customize a user interface for the first user on the first mobile device;

wherein the second device is further configured to communicate with and monitor the first user through the first mobile device;

wherein the second device is further configured to control a plurality of functions of the first mobile device; and wherein the first mobile device is configured to automatically establish a live telephonic and/or voice-over-IP (VOIP) call comprising audio and/or video communications between the first user and the second user, the call being initiated by the second user through the second device and/or the server, and the call being automatically established without interaction by the first user with the first mobile device after the first mobile device authenticates the second user and validates that the second user has initiated the call.

* * * * *

UNITED STATES PATENT AND TRADEMARK OFFICE
CERTIFICATE OF CORRECTION

PATENT NO. : 9,020,476 B2
APPLICATION NO. : 13/612368
DATED : April 28, 2015
INVENTOR(S) : Leipzig et al.

It is certified that error appears in the above-identified patent and that said Letters Patent is hereby corrected as shown below:

Specification

Column 7, line 2, "itself" to read as --itself.--.

Column 11, line 6, "operator" to read as --operator.--.

Column 11, line 11, "range" to read as --range.--.

Column 11, line 14, "confirmation" to read as --confirmation.--.

Column 11, line 38, "206" to read as --206.--.

Column 32, line 57, "links" to read as --links.--.

Signed and Sealed this
Tenth Day of November, 2015

Michelle K. Lee
*Director of the United States Patent and Trademark Office*